(12) United States Patent
Mizuta et al.

(10) Patent No.: US 12,383,134 B2
(45) Date of Patent: Aug. 12, 2025

(54) OPHTHALMIC DEVICE AND OPHTHALMIC OPTICAL SYSTEM

(71) Applicant: NIKON CORPORATION, Tokyo (JP)

(72) Inventors: Masahiro Mizuta, Yokohama (JP); Yasufumi Nishi, Edinburgh (GB)

(73) Assignee: NIKON CORPORATION, Tokyo (JP)

( * ) Notice: Subject to any disclaimer, the term of this patent is extended or adjusted under 35 U.S.C. 154(b) by 442 days.

(21) Appl. No.: 17/707,781

(22) Filed: Mar. 29, 2022

(65) Prior Publication Data

US 2022/0218199 A1 Jul. 14, 2022

Related U.S. Application Data

(63) Continuation of application No. PCT/JP2020/035561, filed on Sep. 18, 2020.

(30) Foreign Application Priority Data

Sep. 30, 2019 (JP) .................. 2019-179050

(51) Int. Cl.
 *A61B 3/12* (2006.01)
 *A61B 3/00* (2006.01)
 *A61B 3/10* (2006.01)

(52) U.S. Cl.
 CPC .............. *A61B 3/12* (2013.01); *A61B 3/0008* (2013.01); *A61B 3/102* (2013.01)

(58) Field of Classification Search
 CPC ......... A61B 3/12; A61B 3/0008; A61B 3/102; A61B 3/1025; A61B 3/117; A61B 3/14;
 (Continued)

(56) References Cited

U.S. PATENT DOCUMENTS

2011/0028953 A1* 2/2011 Raksi .................... A61F 9/0084
606/4
2019/0261853 A1* 8/2019 Williamson ............. A61B 3/14
(Continued)

FOREIGN PATENT DOCUMENTS

EP  2 901 919 A1  8/2015
JP  2015-109988 A  6/2015
(Continued)

OTHER PUBLICATIONS

Office Action issued in corresponding Japanese Patent Application No. 2021-550631, dated Jul. 11, 2023 (5 pages).
(Continued)

*Primary Examiner* — Mohammed A Hasan
(74) *Attorney, Agent, or Firm* — Foley & Lardner LLP

(57) ABSTRACT

An ophthalmic device for observing a subject eye, including: a light source; a scanning section that scans light from the light source; and an objective optical system configured to form a pupil, which has a conjugate relationship with a pupil of the subject eye, at the scanning section, wherein the objective optical system has, in order from the scanning section toward the subject eye, a first lens group that is positive, a second lens group that is positive, and a third lens group that is disposed between the first lens group and the second lens group, and that includes a concave surface configured to diverge light.

8 Claims, 24 Drawing Sheets

(58) Field of Classification Search
CPC ...... A61B 3/1208; G02B 13/18; G02B 21/00; G02B 21/02
USPC ........................................................ 351/204
See application file for complete search history.

(56) References Cited

U.S. PATENT DOCUMENTS

2021/0121058 A1* 4/2021 Furuya .................. A61B 3/102
2022/0079434 A1* 3/2022 Nishi ................... A61B 3/1025
2022/0211265 A1* 7/2022 Nakayama ........... A61B 3/1025

FOREIGN PATENT DOCUMENTS

| JP | 2016-123467 A | 7/2016 |
| JP | 2019-526346 A | 9/2019 |

OTHER PUBLICATIONS

JP Notice of Reasons for Refusal issued in corresponding Japanese Application No. 2023-175553 Dated Feb. 4, 2025 (9 pages).
Office Action issued in corresponding Japanese Patent Application No. 2023-175553 mailed Jun. 24, 2025, with English machine (8 pages).

* cited by examiner

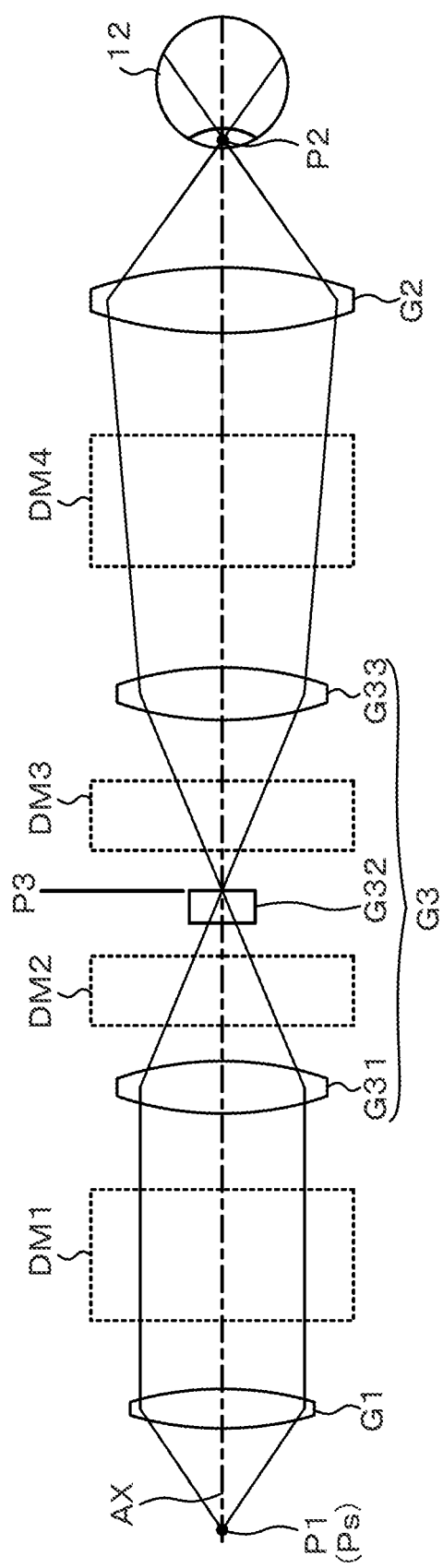

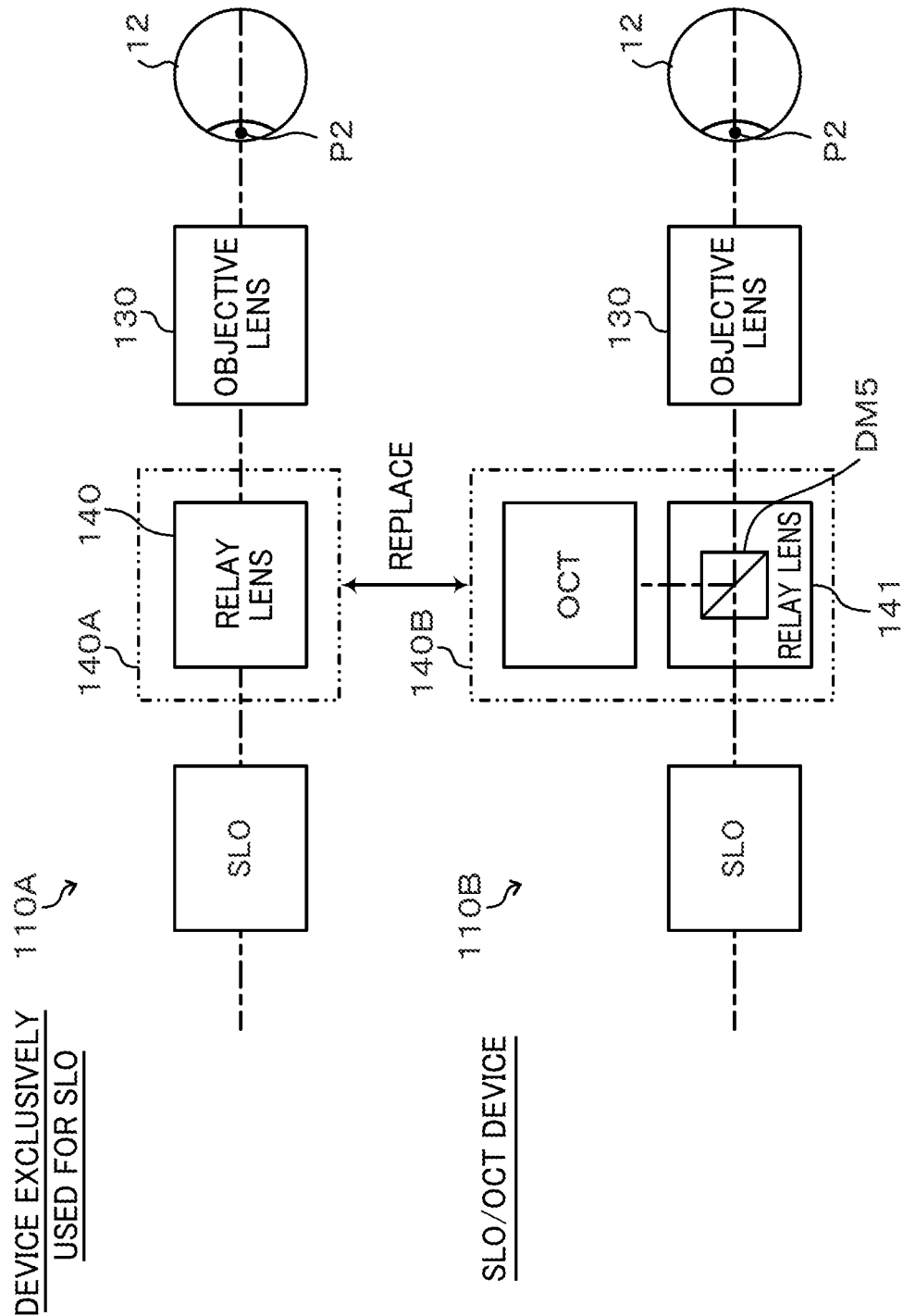

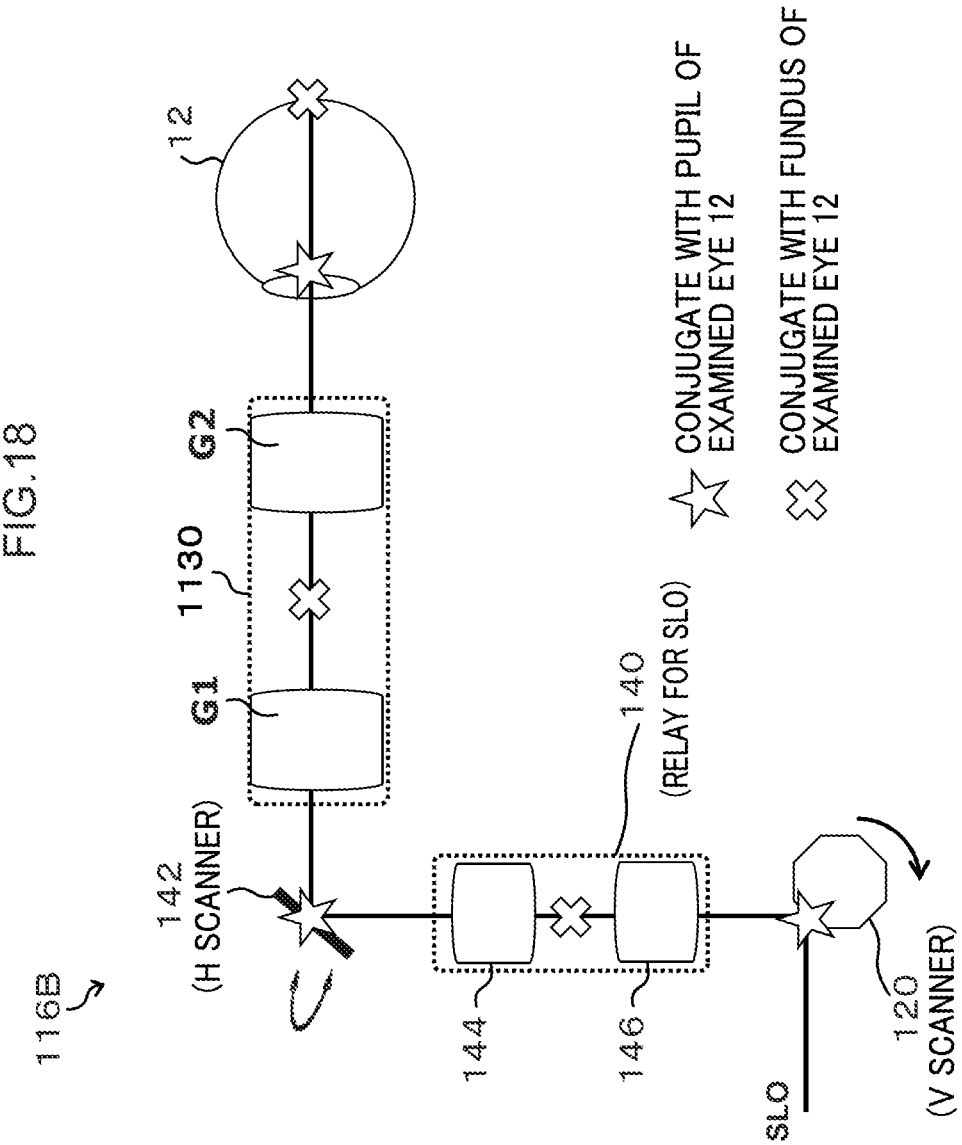

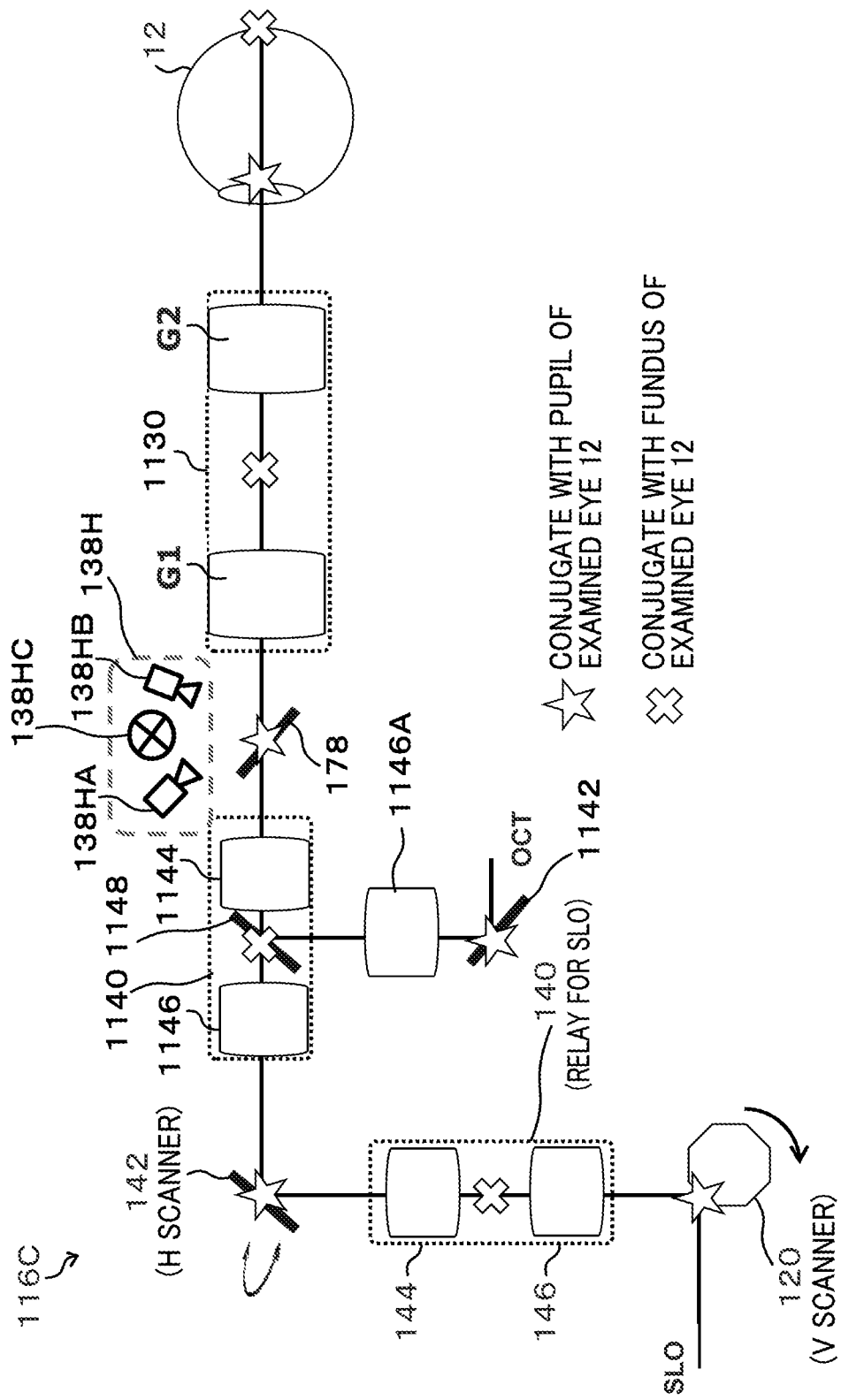

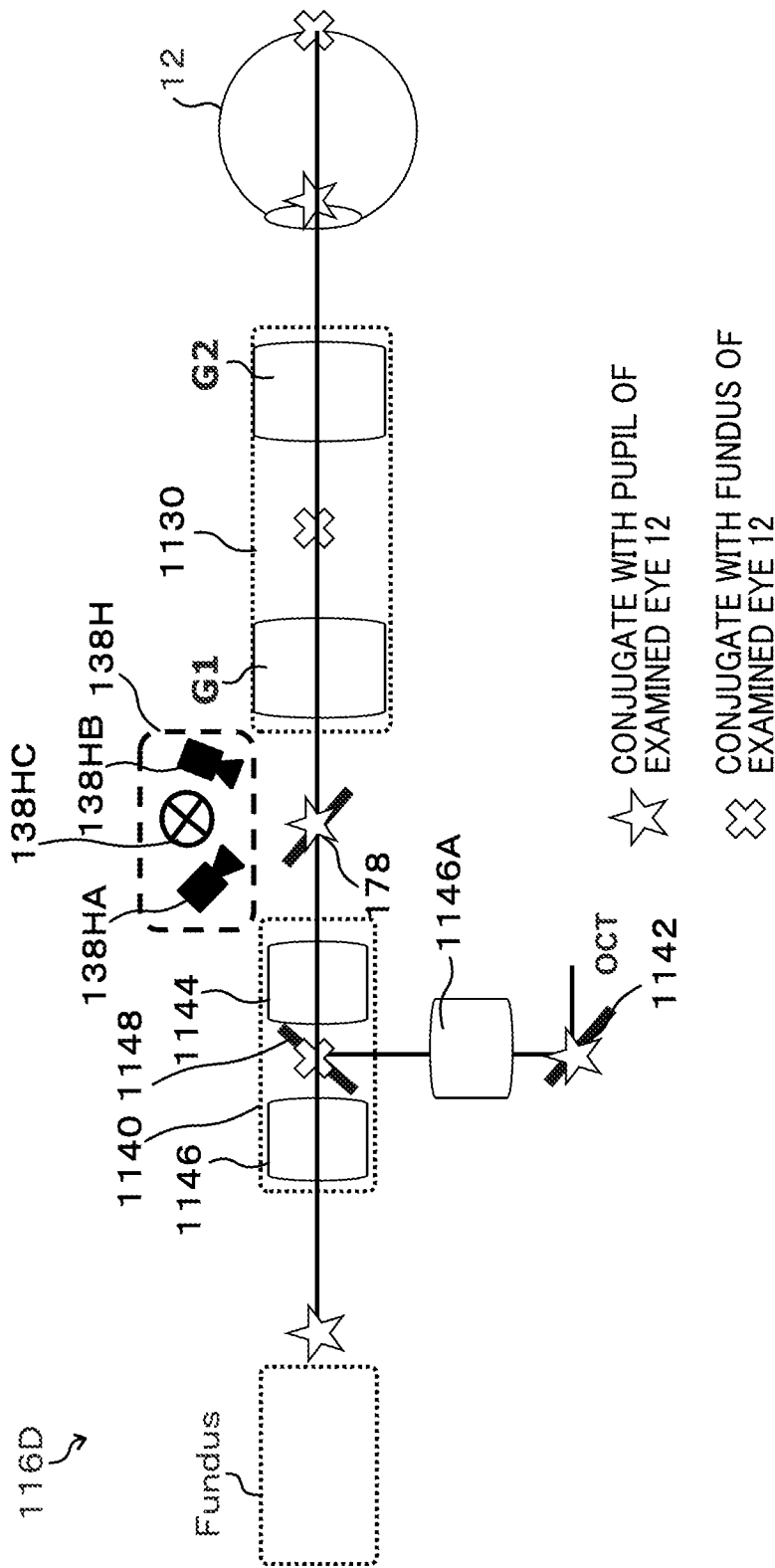

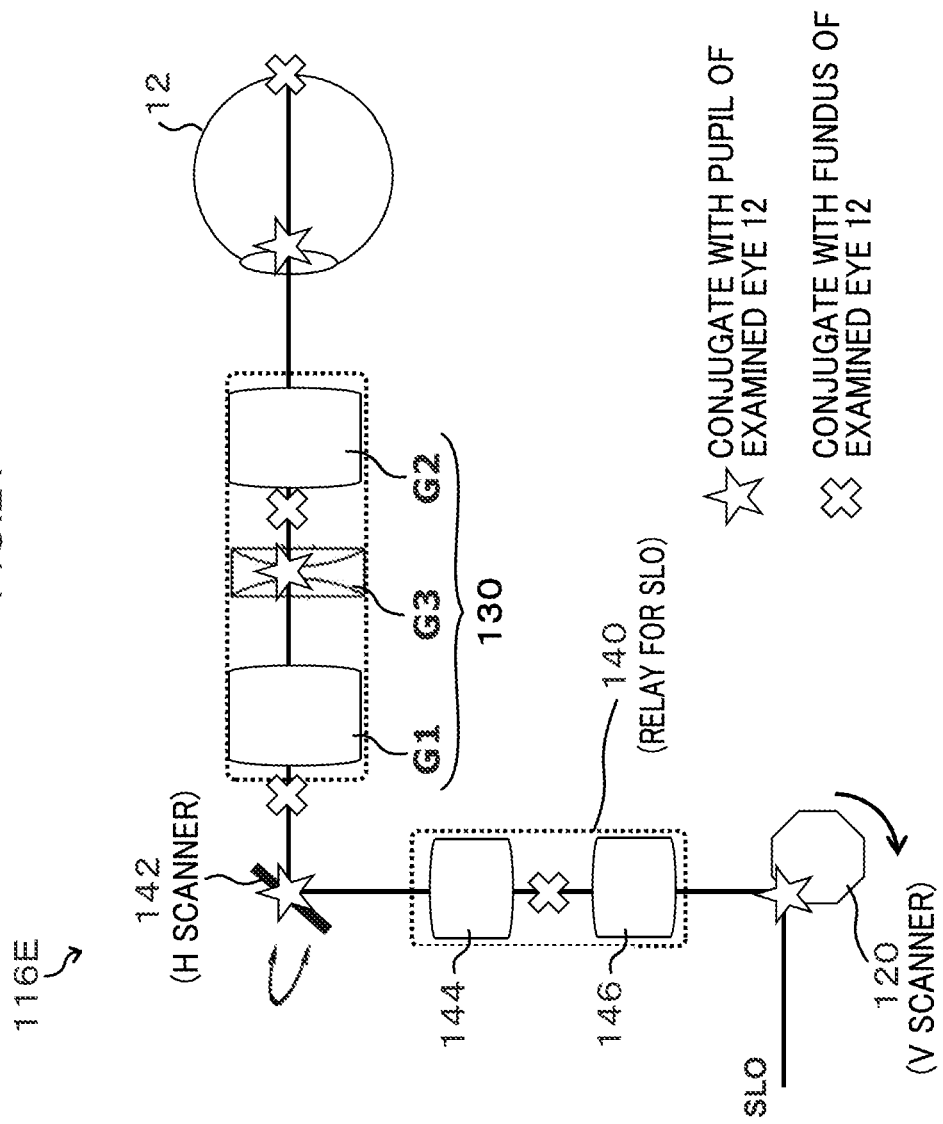

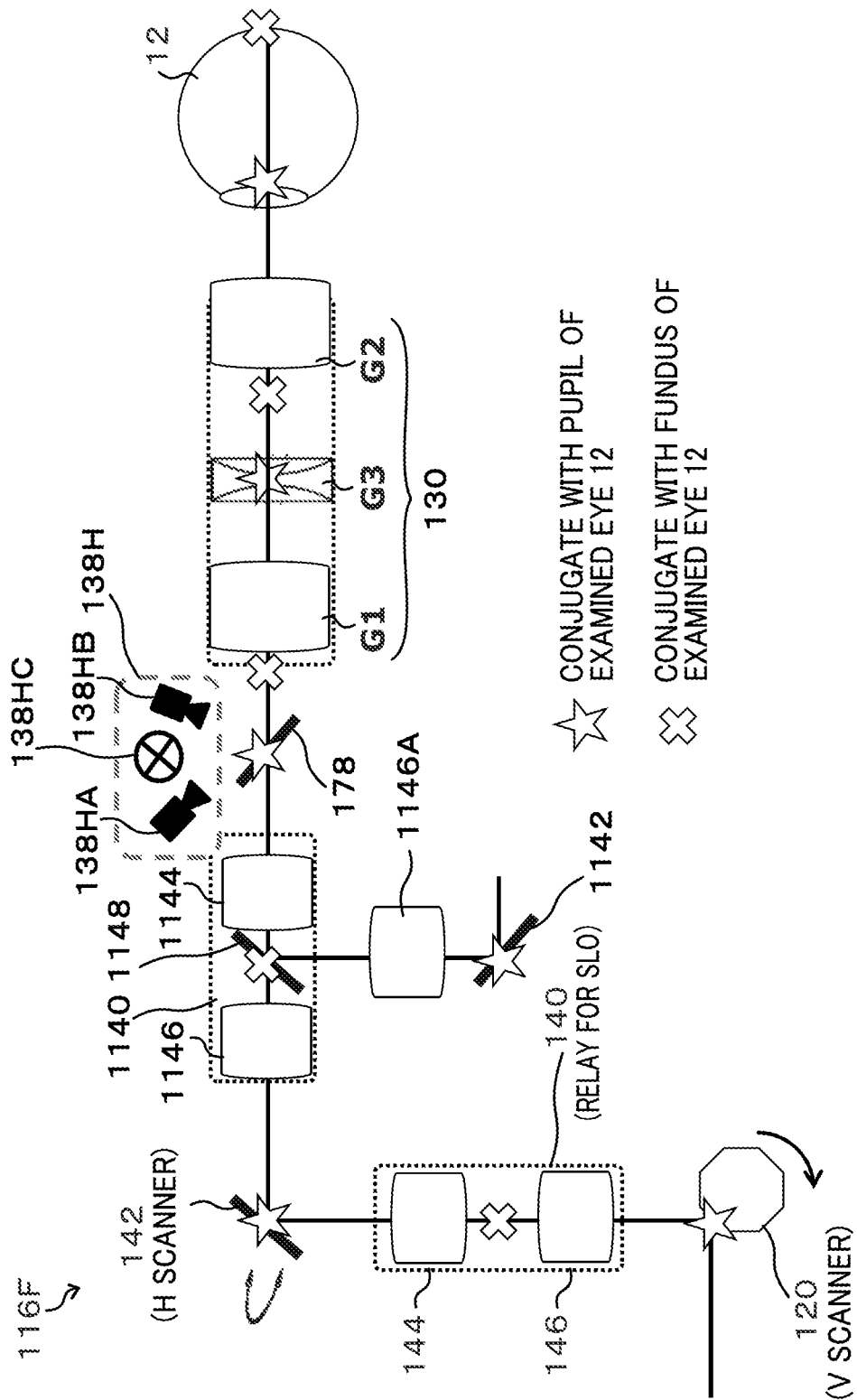

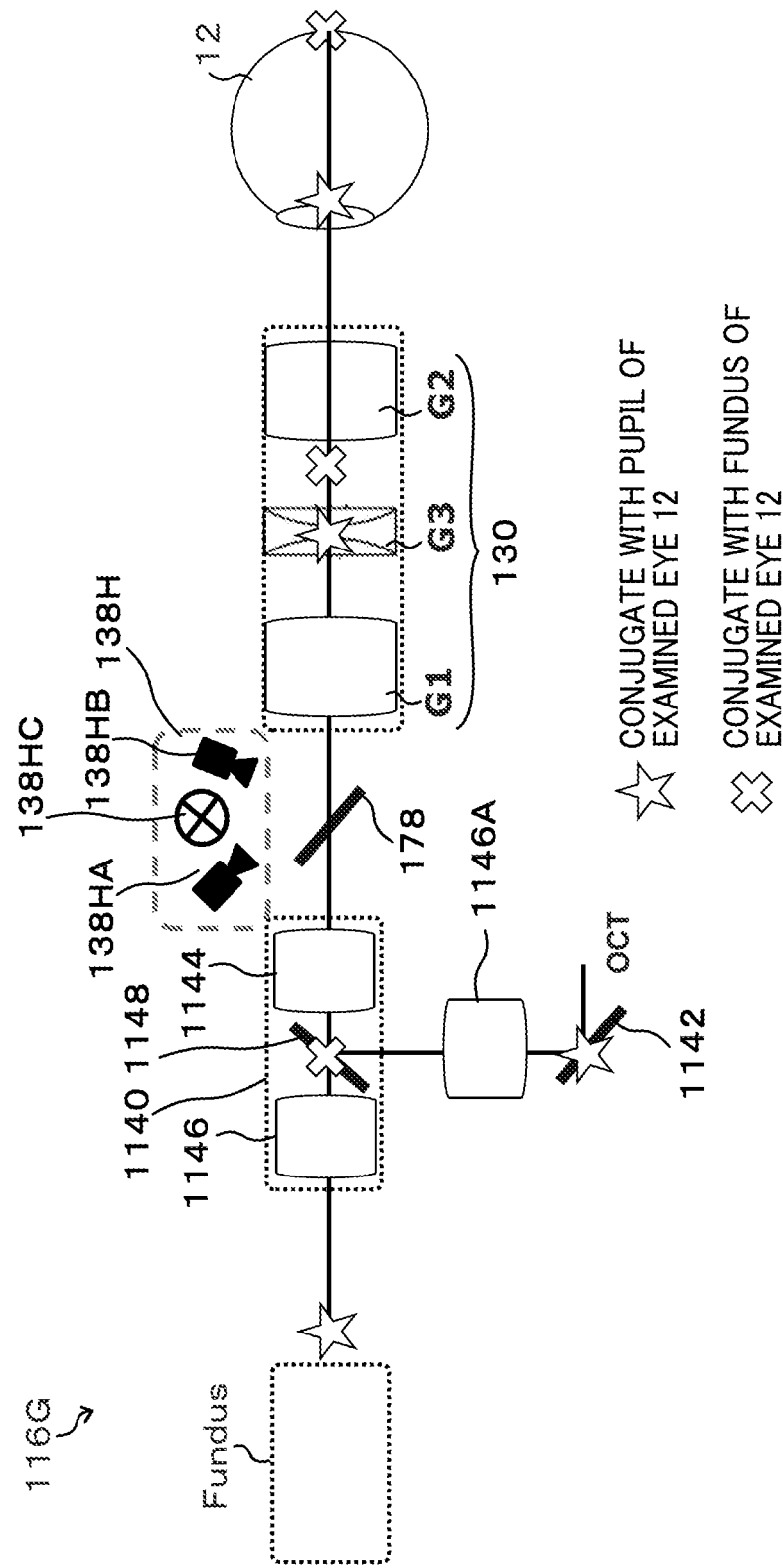

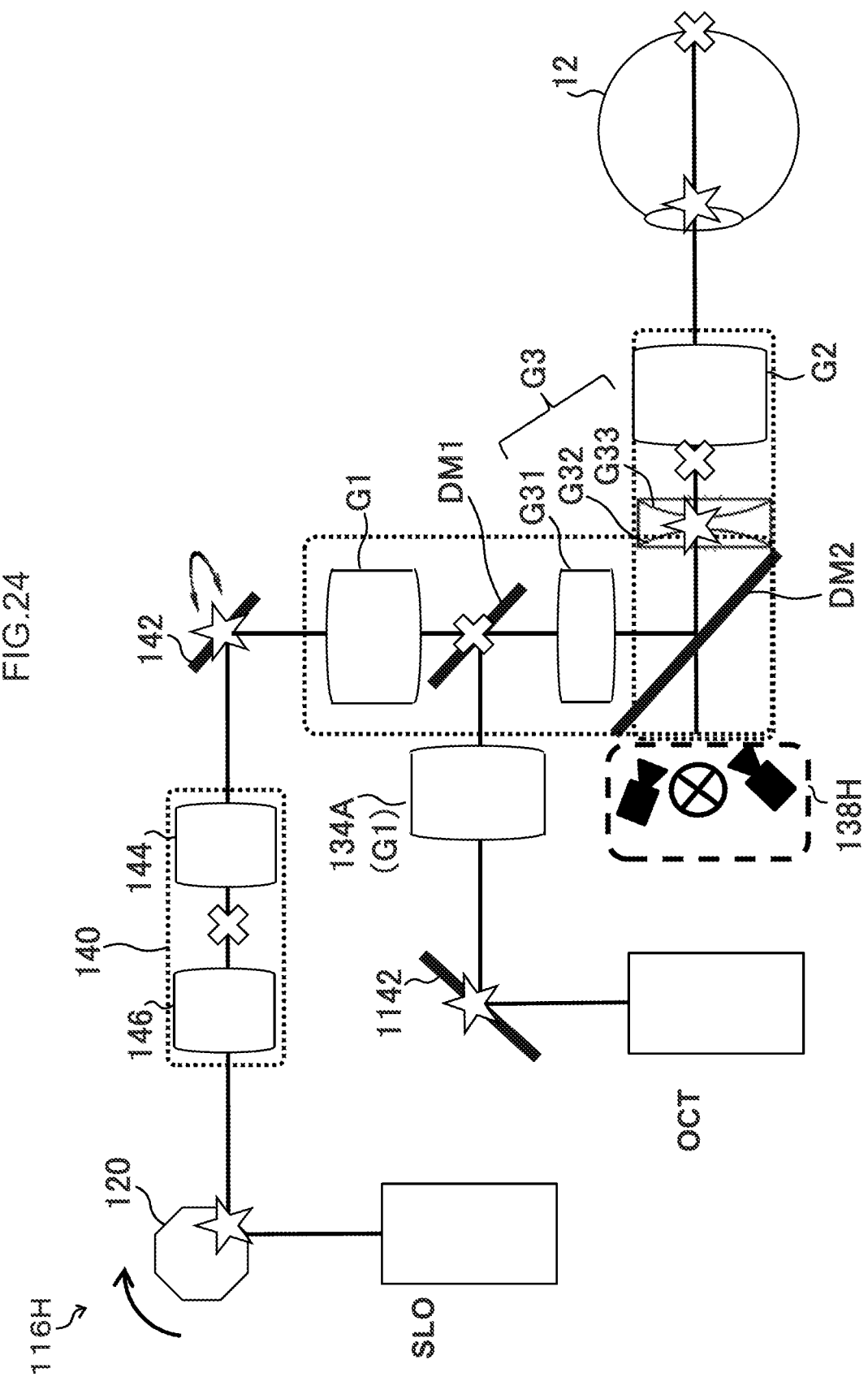

OPHTHALMIC DEVICE AND OPHTHALMIC OPTICAL SYSTEM

CROSS-REFERENCE TO RELATED APPLICATION

This application is a continuation application of International Application No. PCT/JP2020/035561, filed Sep. 18, 2020, the disclosure of which is incorporated herein by reference in its entirety. Further, this application claims priority from Japanese Patent Application No. 2019-179050, filed Sep. 30, 2019, the disclosure of which is incorporated herein by reference in its entirety.

TECHNICAL FIELD

The present invention relates to an ophthalmic device and an ophthalmic optical system.

BACKGROUND ART

European Patent Application Publication No. EP 2901919 A1 discloses an ophthalmic device having an attachment lens for capturing an image of a fundus that has a wide field angle.

SUMMARY

A first aspect of the technique of the present disclosure is an ophthalmic device for observing a subject eye, including: a light source; a scanning section that scans light from the light source; and an objective optical system configured to form a pupil, which has a conjugate relationship with a pupil of the subject eye, at the scanning section, wherein the objective optical system has, in order from the scanning section toward the subject eye, a first lens group that is positive, a second lens group that is positive, and a third lens group that is disposed between the first lens group and the second lens group, and that includes a concave surface configured to diverge light.

A second aspect of the technique of the present disclosure is an ophthalmic optical system for observing a subject eye, including an objective optical system configured to forms a pupil having a conjugate relationship with a pupil of the subject eye, wherein the objective optical system has, in order from a side at which the pupil having a conjugate relationship with the pupil of the subject eye is formed, toward the subject eye, a first lens group that is positive, a second lens group that is positive, and a third lens group that includes a concave surface configured to diverge light and that is disposed between the first lens group and the second lens group.

BRIEF DESCRIPTION OF DRAWINGS

FIG. 16 is a schematic structure drawing of an objective lens that structures an imaging optical system of a fourth embodiment.

FIG. 17 is a schematic structural drawing of an ophthalmic device of a sixth embodiment.

FIG. 18 is a schematic structural drawing of an imaging optical system relating to a first structural example of a seventh embodiment.

FIG. 19 is a schematic structural drawing of an imaging optical system relating to a second structural example of the seventh embodiment.

FIG. 20 is a schematic structural drawing of an imaging optical system relating to a third structural example of the seventh embodiment.

FIG. 21 is a schematic structural drawing of an imaging optical system relating to a fourth structural example of the seventh embodiment.

FIG. 22 is a schematic structural drawing of an imaging optical system relating to a fifth structural example of the seventh embodiment.

FIG. 23 is a schematic structural drawing of an imaging optical system relating to a sixth structural example of the seventh embodiment.

FIG. 24 is a schematic structural drawing of an imaging optical system relating to a seventh structural example of the seventh embodiment.

DESCRIPTION OF EMBODIMENTS

Embodiments of the present disclosure are described in detail hereinafter with reference to the drawings.

First Embodiment

An ophthalmic device 110 relating to a first embodiment of the present disclosure is described hereinafter with reference to the drawings.

Figure 1:
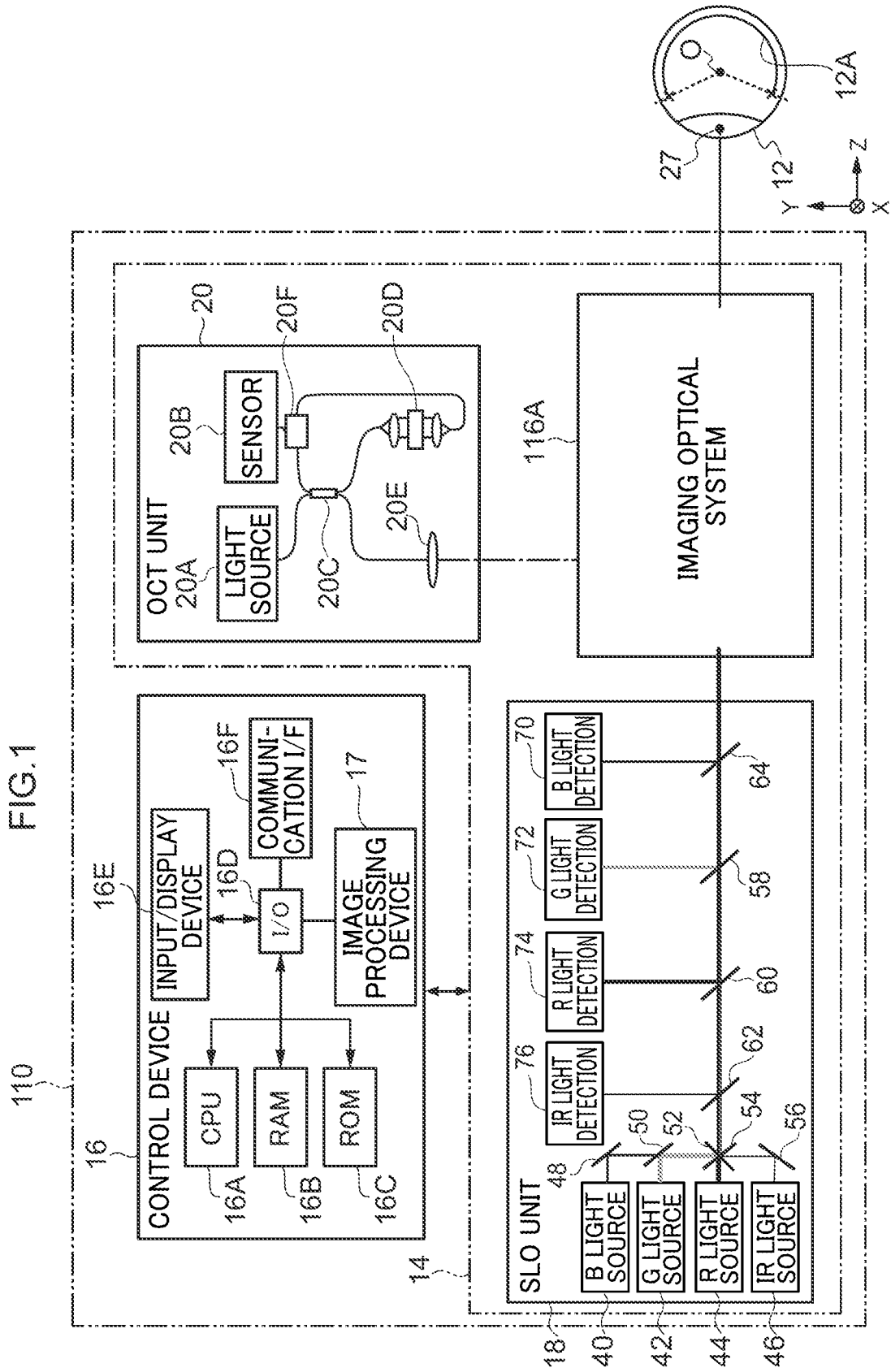
FIG. 1 is a structural drawing of an ophthalmic device of a first embodiment.

The schematic structure of the ophthalmic device 110 is illustrated in FIG. 1.

For convenience of explanation, a scanning laser ophthalmoscope is called "SLO". Further, optical coherence tomography is called "OCT".

Note that the horizontal direction, in a case in which the ophthalmic device 110 is set on a horizontal surface, is the "X direction", the direction orthogonal to the horizontal surface is the "Y direction", and the optical axis direction of an imaging optical system 116A is the "Z direction". The device is placed, with respect to an subject eye, such that the center of pupil d of the subject eye is positioned on the optical axis that is the Z direction. Further, the X direction, the Y direction and the Z direction are orthogonal to one another.

The ophthalmic device 110 includes an imaging device 14 and a control device 16. The imaging device 14 has a SLO unit 18 that acquires an image of the fundus of an subject eye 12, and an OCT unit 20 that acquires a tomographic image of the subject eye 12. Hereinafter, the fundus image that is generated on the basis of the SLO data acquired by the SLO unit 18 is called a SLO image. Further, the tomographic image that is generated on the basis of the OCT data acquired by the OCT unit 20 is called an OCT image. Note that the SLO image is also referred to as a two-dimensional fundus image. Further, the OCT image is also referred to as a fundus tomographic image and an anterior eye portion tomographic image, in accordance with the imaged region of the subject eye 12.

The ophthalmic device 110 is an example of the "ophthalmic device" of the technique of the present disclosure.

The control device 16 has a computer having a CPU (Central Processing Unit) 16A, a RAM (Random Access Memory) 16B, a ROM (Read Only Memory) 16C, and an input/output port (I/O) 16D.

The control device 16 has an input/display device 16E that is connected to the CPU 16A via the I/O port 16D. The input/display device 16E has a graphic user interface that displays the image of the subject eye 12 and receives various instructions from the user. A touch panel display can be used as the input/display device 16E. The control device 16 also has a communication I/F 16F that is connected to the I/O port 16D.

Further, the control device 16 has an image processing device 17 that is connected to the I/O port 16D. The image processing device 17 generates an image of the subject eye 12 on the basis of data obtained by the imaging device 14.

As described above, in FIG. 1, the control device 16 of the ophthalmic device 110 has the input/display device 16E, but the technique of the present disclosure is not limited to this. For example, the control device 16 of the ophthalmic device 110 may not have the input/display device 16E, and may have a separate input/display device that is physically independent of the ophthalmic device 110. In this case, the display device has an image processing processor unit that operates under the control of the CPU 16A of the control device 16. The image processing processor unit may display the SLO image and the like on the basis of image signals that are outputted and instructed from the CPU 16A.

The imaging device 14 operates under the control of the control device 16. The imaging device 14 includes the SLO unit 18, the imaging optical system 116A and the OCT unit 20. The imaging optical system 116A is moved in the X, Y, Z directions by an imaging optical system driving section (not illustrated), under the control of the CPU 16A. The aligning (positioning) of the imaging device 14 and the subject eye 12 may be carried out, for example, by moving not merely the imaging device 14, but the entire ophthalmic device 110 in the X, Y, Z directions.

A SLO system is realized by the control device 16, the SLO unit 18 and the imaging optical system 116A that are illustrated in FIG. 1.

The SLO unit 18 has plural light sources. For example, as illustrated in FIG. 1, the SLO unit 18 has a light source 40 of B light (blue color light), a light source 42 of G light (green color light), a light source 44 of R light (red color light), and a light source 46 of IR light (infrared light (e.g., near infrared light)). The lights that exit from the respective light sources 40, 42, 44, 46 are directed toward the same optical path via respective optical members 48, 50, 52, 54, 56. The optical members 48, 56 are mirrors, and the optical members 50, 52, 54 are beam splitters. The B light is guided via the optical members 48, 50, 54 to the optical path of the imaging optical system 116A. The G light is guided via the optical members 50, 54 to the optical path of the imaging optical system 116A. The R light is guided via the optical members 52, 54 to the optical path of the imaging optical system 116A. The IR light is guided via the optical members 56, 52 to the optical path of the imaging optical system 116A. Note that LED light sources or laser light sources can be used as the light sources 40, 42, 44, 46. Note that an example using laser light sources is described hereinafter. Total reflection mirrors can be used as the optical members 48, 56. Further, dichroic mirrors, half mirrors or the like can be used as the optical members 50, 52, 54.

The light sources 40, 42, 44, 46 are examples of the "light source" of the technique of the present disclosure.

The SLO unit 18 is structured so as to be able to be switched between various light-emitting modes such as a light-emitting mode in which G light, R light, B light and IR light are respectively emitted independently, a light-emitting mode in which these lights are all emitted simultaneously or some thereof are emitted simultaneously, and the like. In the example illustrated in FIG. 1, the four light sources that are the light source 40 of B light (blue color light), the light source 42 of G light, the light source 44 of R light, and the light source 46 of IR light are provided, but the technique of the present disclosure is not limited to this. For example, the SLO unit 18 may further have a light source of white light. In this case, in addition to the above-described various light-emitting modes, a light-emitting mode in which only white light is emitted, or the like, may be set.

The laser light that is incident on the imaging optical system 116A from the SLO unit 18 is scanned in the X direction and the Y direction by scanning sections (120, 142) that are described later. The scanning light is illuminated, via pupil 27, onto the posterior eye portion (e.g., the fundus) of the subject eye 12. The reflected light that is reflected by the fundus is incident, via the imaging optical system 116A, onto the SLO unit 18.

The scanning sections (120, 142) are examples of the "scanning sections" of the technique of the present disclosure.

The reflected light that is reflected at the fundus of the subject eye 12 is detected by light detecting elements 70, 72, 74, 76 that are provided at the SLO unit 18. In the present embodiment, the SLO unit 18 has the B light detecting element 70, the G light detecting element 72, the R light detecting element 74 and the IR light detecting element 76, in correspondence with the plural light sources, i.e., the B light source 40, the G light source 42, the R light source 44 and the IR light source 46. The B light detecting element 70 detects the B light that is reflected at the beam splitter 64. The G light detecting element 72 detects the G light that is transmitted through the beam splitter 64 and reflected at the beam splitter 58. The R light detecting element 74 detects the R light that is transmitted through the beam splitters 64, 58 and is reflected at the beam splitter 60. The IR light detecting element 76 detects the G light that is transmitted through the beam splitters 64, 58, 60 and is reflected at the beam splitter 62. APDs (avalanche photodiodes) are examples of the light detecting elements 70, 72, 74, 76.

Under the control of the CPU 16A, the image processing device 17 generates SLO images corresponding to the respective colors, by using the signals detected by the B light detecting element 70, the G light detecting element 72, the R light detecting element 74 and the IR light detecting element 76, respectively. The SLO images corresponding to the respective colors are a B-SLO image generated by using the signals detected by the B light detecting element 70, a G-SLO image generated by using the signals detected by the G light detecting element 72, an R-SLO image generated by using the signals detected by the R light detecting element 74, and an IR-SLO image generated by using the signals detected by the IR light detecting element 76. Further, in the case of the light-emitting mode in which the B light source 40, the G light source 42 and the R light source 44 emit light simultaneously, an RGB-SLO image may be synthesized from the B-SLO image, the G-SLO image and the R-SLO image that are generated by using the respective signals detected by the R light detecting element 74, the G light detecting element 72 and the B light detecting element 70. Further, in the case of the light-emitting mode in which the G light source 42 and the R light source 44 emit light simultaneously, an RG-SLO image may be synthesized from the G-SLO image and the R-SLO image that are generated by using the respective signals detected by the R light detecting element 74 and the G light detecting element 72. Although an RG-SLO image is used as the SLO image in the first embodiment, the technique of the present disclosure is not limited to this, and another SLO image can be used.

Dichroic mirrors, half mirrors or the like can be used for the beam splitters 58, 60, 62, 64.

The OCT system is a three-dimensional image acquiring device that is realized by the control device 16, the OCT unit 20 and the imaging optical system 116A that are illustrated in FIG. 1. The OCT unit 20 includes a light source 20A, a sensor (detecting element) 20B, a first optical coupler 20C, a reference optical system 20D, a collimator lens 20E and a second optical coupler 20F.

The light source 20A emits light for optical coherence tomography. For example, a super luminescent diode (SLD) can be used as the light source 20A. The light source 20A generates low interference light of a broadband light source that has a wide spectral width. The light that exits from the light source 20A is split at the first optical coupler 20C. One divisional light is made into parallel light at the collimator lens 20E as measurement light, and thereafter, is made incident on the imaging optical system 116A. The measurement light is scanned in the X direction and the Y direction by scanning sections (148, 142) that are described later. The scanning light is illuminated onto the anterior eye portion of the subject eye, or onto the posterior eye portion via the pupil 27. The measurement light that is reflected by the anterior eye portion or the posterior eye portion goes through the imaging optical system 116A and is made incident on the OCT unit 20, and, via the collimator lens 20E and the first optical coupler 20C, is incident on the second optical coupler 20F. Note that, in the present embodiment, an SD-OCT using an SLD is given as an example of the light source 20A, but the technique of the present disclosure is not limited to this, and an SS-OCT that uses a wavelength sweeping light source may be employed instead of an SLD.

The other light, which exits from the light source 20A and is branched-off at the first optical coupler 20C, is incident on the reference optical system 20D as reference light, and goes through the reference optical system 20D and is incident on the second optical coupler 20F.

The measurement light (returned light) that is reflected and scattered at the subject eye 12, and the reference light, are combined at the second optical coupler 20F, and interference light is generated. The interference light is detected at the sensor 20B. On the basis of a detection signal (OCT data) from the sensor 20B, the image processing device 17 generates a tomographic image of the subject eye 12.

In the first embodiment, the OCT system generates a tomographic image of the anterior eye portion or the posterior eye portion of the subject eye 12.

The anterior eye portion of the subject eye 12 is the portion that includes, for example, the cornea, the iris, the corner angle, the lens, the ciliary body and a portion of the vitreous body, as the anterior eye segment. The posterior eye portion of the subject eye 12 is the portion that includes, for example, the remaining portion of the vitreous body, the retina, the choroid and the sclera, as the posterior eye segment. Note that the vitreous body that belongs to the anterior eye portion is the portion of the vitreous body that is at the cornea side, with the border being the X-Y plane that passes through the point of the lens that is nearest to the center of the eyeball. The vitreous body that belongs to the posterior eye portion is the portion of the vitreous body that is other than the vitreous body belonging to the anterior eye portion.

In a case in which the anterior eye portion of the subject eye 12 is the region that is the object of imaging, the OCT system generates a tomographic image of the cornea for example. Further, in a case in which the posterior eye portion of the subject eye 12 is the region that is the object of imaging, the OCT system generates a tomographic image of the retina for example.

Figure 2:
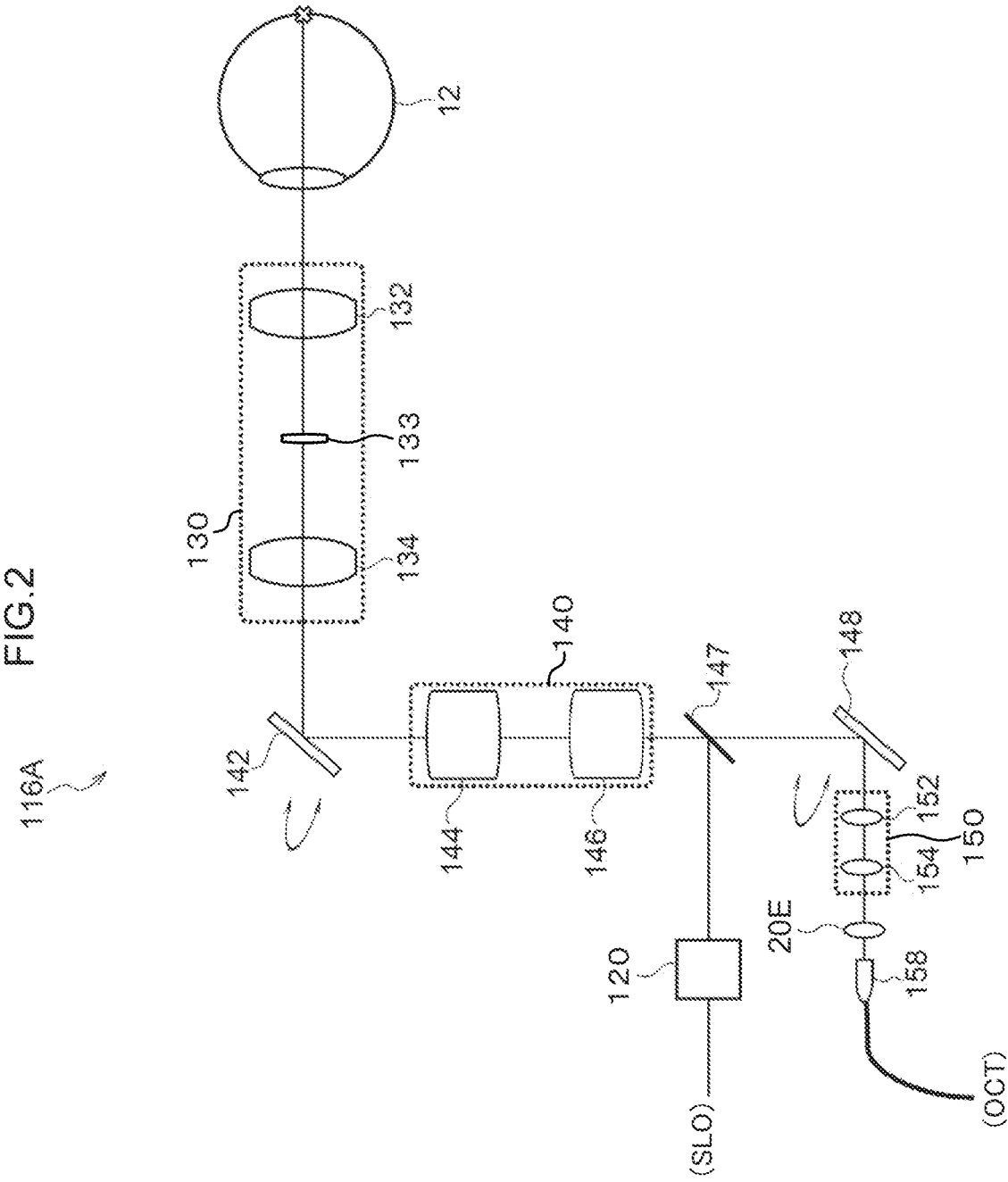
FIG. 2 is a schematic structural drawing of an imaging optical system of the first embodiment.

The schematic structure of the imaging optical system 116A is illustrated in FIG. 2. The imaging optical system 116A has an objective lens 130, the horizontal scanning section 142, a relay lens device 140, a beam splitter 147, the vertical scanning sections 120, 148, a focus adjusting device 150 and the collimator lens 20E that are disposed in that order from the subject eye 12 side.

For example, dichroic mirrors, half mirrors or the like can be used as beam splitters 178, 147.

The horizontal scanning section 142 is an optical scanner that scans, in the horizontal direction, the laser light of SLO and the measurement light of OCT that are incident via the relay lens device 140. In the present embodiment, the horizontal scanning section 142 is shared by the SLO optical system and the OCT optical system, but the technique of the present disclosure is not limited to this. A horizontal scanning section may be provided for each of the SLO optical system and the OCT optical system.

The collimator lens 20E makes, into parallel light, the measurement light that exits from end portion 158 of a fiber through which the light exiting from the OCT unit 20 advances.

The focus adjusting device 150 has plural lenses 152, 154. The focus adjusting device 150 adjusts the focus position of the measurement light at the subject eye 12 by moving the plural lenses 152, 154 respectively in the optical axis direction appropriately in accordance with the region to be imaged at the subject eye 12. Note that, although not illustrated, in a case in which a focus detecting device is provided, an autofocus device can be realized by driving the lenses 152, 154 by the focus adjusting device in accordance with the state of focal point detection, and carrying out focusing automatically.

The vertical scanning section 148 is an optical scanner that scans, in the vertical direction, the measurement light that is incident thereon via the focus adjusting device 150.

The vertical scanning section 120 is an optical scanner that scans, in the vertical direction, the laser light that is incident thereon from the SLO unit 18.

The relay lens device 140 has plural lenses 144, 146 that have positive power. The relay lens device 140 is structured by the plural lenses 144, 146 such that the positions of the vertical scanning sections 148, 120 and the position of the horizontal scanning section 142 are conjugate. More specifically, the relay lens device 140 is structured such that the central positions of the angular scanning of the both scanning sections are conjugate.

The beam splitter 147 is disposed between the relay lens device 140 and the vertical scanning section 148. The beam splitter 147 is an optical member that combines the SLO optical system and the OCT optical system, and reflects the SLO light, which exits from the SLO unit 18, toward the relay lens device 140, and transmits the measurement light, which exits from the OCT unit 20, toward the relay lens device 140. The measurement light that exits from the OCT unit 20 is two-dimensionally scanned by the vertical scanning section 148 and the horizontal scanning section 142. Further, the light that exits from the SLO unit 18 is two-dimensionally scanned by the vertical scanning section 120 and the horizontal scanning section 142 that structure the SLO optical system. The OCT measurement light and the SLO laser light that are scanned two-dimensionally are respectively made incident onto the subject eye 12 via the objective lens 130 that structures a shared optical system. The SLO laser light that is reflected at the subject eye 12 goes through the objective lens 130, the horizontal scanning section 142, the relay lens device 140, the beam splitter 147 and the vertical scanning section 120, and is made incident on the SLO unit 18. Further, the OCT measurement light that has gone through the subject eye 12 goes through the objective lens 130, the horizontal scanning section 142, the relay lens device 140, the beam splitter 147, the vertical scanning section 148, the focus adjusting device 150 and the collimator lens 20E, and is made incident on the OCT unit 20.

For example, resonant scanners, galvano mirrors, polygon mirrors, rotating mirrors, dove prisms, double dove prisms, rotation prisms, MEMS mirror scanners, acousto-optic elements (AOMs) and the like are suitably used as the horizontal scanning section 142 and the vertical scanning sections 120, 148. In the present embodiment, a galvano mirror is used as the vertical scanning section 148, and further, a polygon mirror is used as the vertical scanning section 120. Note that, in a case in which a two-dimensional optical scanner such as a MEMS mirror scanner or the like is used instead of an optical scanner such as a polygon mirror or a galvano mirror or the like, the incident light can be angle-scanned two-dimensionally by that reflecting element, and therefore, the relay lens device 140 may be eliminated.

The objective lens 130 has, in order from the horizontal scanning section 142 side, a first lens group 134 and a second lens group 132. At least the second lens group 132 is, overall, a positive lens group having positive power. In the first embodiment, the first lens group 134 as well is, overall, a positive lens group having positive power. Each of the first lens group 134 and the second lens group 132 has at least one positive lens. In a case in which each of the first lens group 134 and the second lens group 132 has plural lenses, the first lens group 134 and the second lens group 132 may include a negative lens, provided that each of the first lens group 134 and the second lens group 132 has positive power overall.

Further, the objective lens 130 of the present disclosure has a third lens group 133 in the space between the first lens group 134 and the second lens group 132.

The first lens group 134 is an example of the "first lens group" of the technique of the present disclosure, the second lens group 132 is an example of the "second lens group" of the technique of the present disclosure, and the third lens group 133 is an example of the "third lens group" of the technique of the present disclosure.

The first lens group 134 and the second lens group 132 that structure the objective lens 130 are separated by the longest air gap on optical axis AX between lens surfaces at the objective lens 130. The third lens group 133 is disposed in the space of this longest air gap.

As a result, the gap between the first lens group 134 and the third lens group 133, and the air gap between the third lens group 133 and the second lens group 132, are the largest air gap and the second largest air gap among the lens gaps of the entire objective lens 130. In a case in which the third lens group 133 that is the intermediate group is disposed at the subject eye 12 side between the first lens group 134 and the second lens group 132, the gap between the first lens group 134 and the third lens group 133 is the largest. In a case in which the third lens group 133 is disposed at the scanning section side, the gap between the third lens group 133 and the second lens group 132 is the largest. Note that, even if there is a glass plate that does not have power at a position between the first lens group 134 and the second lens group 132, the glass plate is not considered to be a lens that belongs to either the first lens group 134 or the second lens group 132, and it is considered that the first lens group 134 and the second lens group 132 are separated by the longest air gap. This longest air gap is convenient for providing a combining section that has light combining and light splitting functions such as a dichroic mirror or the like.

Note that, although not illustrated, the imaging optical system 116A can have an optical module that includes a fixation lamp that provides a fixation target, a camera and an illumination device. Such an optical module can be disposed so as to be combined into the optical path of the imaging optical system 116A by a beam splitter or the like.

The imaging optical system 116A has the objective lens 130 that functions as a posterior eye portion observing optical system that observes the posterior eye portion that includes at least the fundus of the subject eye 12. Due to the imaging optical system 116A having an optical module (not illustrated) for anterior eye portion observation that can be inserted onto and removed from the optical path of the objective lens 130, and the optical module for anterior eye portion observation being placed on the optical path of the objective lens 130, the imaging optical system 116A can be switched from the posterior eye portion observing optical system to the anterior eye portion observing optical system. In the first embodiment, the imaging optical system 1116A is described with the focus being on the posterior eye portion observing optical system, and description of the imaging optical system 116A, which functions as an anterior eye portion observing optical system in which an optical module for anterior eye portion observation is placed on the optical path of the objective lens 130, is omitted.

Figure 3:
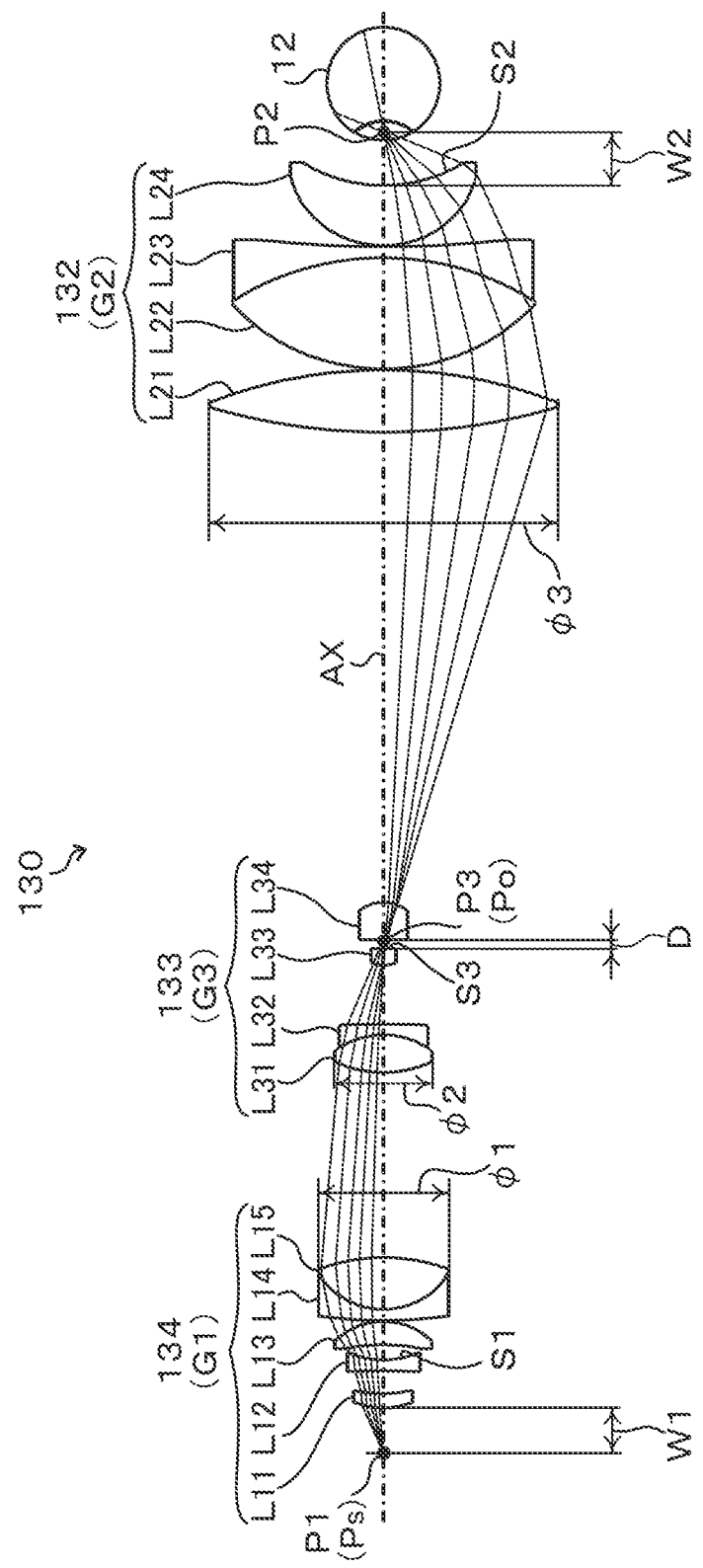
FIG. 3 is a structural drawing of an objective lens that structures the imaging optical system.

An example of the concrete structure of the objective lens 130, which structures the imaging optical system 116A that functions as a posterior eye portion observing optical system that observes the posterior eye portion of the subject eye 12, is illustrated in FIG. 3.

The scanning center positions of the horizontal scanning section 142 and the vertical scanning section 148 illustrated in FIG. 2 correspond to scanning center position Ps that is illustrated in FIG. 3. The objective lens 130 is disposed such that this scanning center position Ps is conjugate with pupil position P2 of the subject eye 12. Namely, this is a structure in which the scanning center position Ps of the scanning sections coincides with the pupil position (hereinafter called pupil conjugate position P1) that has a conjugate relationship with the pupil position P2 of the subject eye 12. In a SLO optical system, the SLO laser light that is scanned by the vertical scanning section 120 and the horizontal scanning section 142 goes through the objective lens 130 and is angle-scanned two-dimensionally with the pupil position P2 of the subject eye 12 being the center. As a result, the collected point of the SLO laser light is scanned two-dimensionally at the fundus of the subject eye 12.

Further, at the OCT optical system as well, similarly, the measurement light that is scanned by the vertical scanning section 148 and the horizontal scanning section 142 goes through the objective lens 130 and is angle-scanned two-dimensionally with the pupil position P2 of the subject eye 12 being the center. As a result, the collected point of the measurement light is scanned two-dimensionally at the fundus of the subject eye 12. In a case of observing the posterior eye portion, a fundus two-dimensional image is acquired by the SLO unit 18, and a fundus tomographic image is acquired by the OCT unit 20.

The important point in such a structure is that the light that is supplied to the respective SLO and OCT scanning sections is a parallel light bundle, and the parallel light bundle is angle-scanned at the pupil P2 of the subject eye by the angular scanning by the scanning section. Therefore, the objective lens 130 must structure an afocal system on the whole. Further, the scanning angle of the parallel light bundle at the pupil P2 of the subject eye is determined by the scanning angles at the scanning sections and the angular magnification of the objective lens 130. In this case, for paraxial angular magnification M of the objective lens 130, a range of around 1.5× to 5× (1.5 ☐M ☐5) is preferable.

An intermediate pupil position P3 is formed in the third lens group 133 (G3) that serves as an intermediate group. The light beams illustrated in FIG. 3 are the respective main light beams of scanning light bundles of five angles up to the maximum angle that are incident on the pupil P2 of the subject eye 12, and this is clear from the fact that these main light beams intersect in the third lens group 133 (G3).

Specifically, the objective lens 130 functions as an optical system that transfers the scanning center position Ps of the scanning section to the pupil (the pupil position P2) of the subject eye 12, and has plural lens groups including the first lens group 134 (G1) that is positive and the second lens group 132 (G2) that is positive. The objective lens 130 is structured such that the position (hereinafter called the intermediate pupil position P3), which is in a conjugate relationship with the scanning center position Ps of the scanning section, is formed between the first lens group 134 and the second lens group 132. Namely, the scanning center position Ps is the pupil conjugate position P1, and is conjugate with the pupil position P2 of the subject eye 12 and the intermediate pupil position P3, and the first lens group 134 is a positive lens group, and the second lens group 132 also is a positive lens group. In the example illustrated in FIG. 3, the first lens group (G1) includes, in order from the pupil conjugate position P1 side that is the scanning section side (e.g., the nearest horizontal scanning section 142 side) toward the subject eye 12 side, a positive meniscus lens L11 whose convex surface faces the scanning section side, a negative lens L12 whose concave surface faces the scanning section side, a positive meniscus lens L13 whose concave surface faces the scanning section side, and a lens component (a cemented lens of negative lens L14 and positive lens L15) that is positive at the scanning section side. Note that "lens component" in the present specification means a lens in which there are two interfaces that contact air on the optical axis. One lens component means one single lens, or one cemented lens that is structured by plural lenses being cemented together. A case in which the lens component of the first lens group 134 is a cemented lens as illustrated is effective for chromatic aberration correction, but the lens component of the first lens group 134 can be made to be a single lens in a case in which the wavelength region of the lights that are used is relatively narrow.

The second lens group 132 (G2) includes, in order from the scanning section side toward the subject eye side, a positive lens L21, a lens component (a cemented lens of a positive lens L22 and a negative lens L23) that is shaped as a positive meniscus whose convex surface faces the scanning section side, and a positive meniscus lens L24 whose convex surface faces the scanning section side. A case in which the meniscus-shaped lens component of the second lens group 132 is a cemented lens as illustrated is effective for chromatic aberration correction, but the lens component of the second lens group 132 can be made to be a single lens in a case in which the wavelength region of the lights that are used is relatively narrow.

The third lens group 132 (G3) includes, in order from the scanning section side toward the subject eye side, a lens component (e.g., a cemented lens of a positive lens L31 and a negative lens L32) that is positive or negative at the scanning section side, a meniscus lens L33 whose convex surface faces the scanning section side, and a meniscus lens L34 whose concave surface faces the scanning section side. The third lens group 133 is formed so as to include the intermediate pupil position P3. It is preferable for there to be a structure in which the conjugate point P3 of the pupil is formed between the negative meniscus lens L33 whose convex surface faces the scanning section side and the meniscus negative lens L34 whose concave surface faces the scanning section side, i.e., at a position sandwiched between the concave surfaces of the both lenses.

Note that the first lens group 134 (G1) and the second lens group 132 (G2) both have positive refractive powers, but it suffices for the third lens group 133 (G3) that serves as an intermediate group to have a strong diverging surface in the vicinity of the intermediate pupil position that is extremely effectively in correcting aberration. Although it is preferable for the refractive power of the third lens group 133 (G3) to mainly be positive, the refractive power can also be negative.

Here, due to the imaging optical system 116A forming a wide angle optical system, observation at a wide field of view FOV at the fundus of the subject eye 12 is realized. The field of view FOV means the range that can be imaged by the imaging device 14. The field of view FOV can be expressed as the viewing angle. In the first embodiment, the viewing angle can be prescribed by the internal illumination angle and the external illumination angle. The external illumination angle is the illumination angle in which the illumination angle of the light bundle, which is illuminated from the ophthalmic device 110 toward the subject eye 12, is prescribed by using the pupil 27 as the reference. Further, the internal illumination angle is the illumination angle in which the illumination angle of the light bundle, which is illuminated toward the fundus of the subject eye 12, is prescribed by using eyeball center O as the reference. The external illumination angle and the internal illumination angle have a corresponding relationship. For example, in a case in which the external illumination angle is 120°, the internal illumination angle corresponds to approximately 160°.

In a case of forming the objective lens 130 that has a large wide angle (e.g., a UWF (Ultra Wide Field) exceeding 100°) in order to observe the subject eye 12 in a wide field of view FOV, aberration correction of the objective lens 130 is important, and there is the tendency for curving of the image surface, e.g., the Petzval sum, to increase. Thus, in the first embodiment, at the ultra wide field objective lens 130, an optical system that can suppress curving of the image surface, e.g., the Petzval sum, is provided.

Specifically, in the first embodiment, as an example of the ophthalmic optical system of the present disclosure, the objective lens 130 has the first lens group 134 and the second lens group 132 that respectively have positive power, and the third lens group 133, which includes a concave surface that diverges light, is disposed between the first lens group 134 and the second lens group 132. Namely, it suffices to include a concave surface, which is a surface (a diverging surface) at which the direction in which light diverges is from the glass material into a space, between the positive first lens group 134 and the positive second lens group 132. In other words, the objective lens 130 has the positive first lens group 134 and the positive second lens group 132 in that order from the scanning section side toward the subject eye 12, and the third lens group 133, which includes a concave surface that diverges light, is disposed between the first lens group 134 and the second lens group 132.

By forming the objective lens 130 in this way, an increase in the Petzval sum of the objective lens 130 can at least be suppressed.

By the way, in a case of forming the objective lens 130 that has a large wide angle (e.g., an ultra wide field (UWF) exceeding 100°) in order to observe the subject eye 12 in a wide field of view FOV, the lens diameter increases in accordance with the field angle increasing. Further, accompanying the increase in the lens diameter, the total amount of the glass material of the lens increases, and the entire weight of the objective lens also increases. Moreover, in a case of forming the objective lens 130, aberration correction of the objective lens 130 is important, and the operation of the lens system with respect to the pupil that is the object at the objective lens greatly affects the aberration correction of the objective lens 130. Thus, in the first embodiment, an optical system that makes it possible to reduce the maximum aperture of the objective lens 130 is provided. Specifically, in the first embodiment, as an example of the ophthalmic optical system of the present disclosure, by forming the objective lens 130 so as to incorporate an intermediate pupil into the objective lens 130, the maximum aperture of the objective lens 130 is reduced.

In the first embodiment, at the objective lens 130, the intermediate pupil, which is different than the pupil that has a conjugate relationship with the pupil of the subject eye 12, is formed between the first lens group 134 and the second lens group 132, and the third lens group 133 is disposed so as to include the position of the intermediate pupil.

Due to the objective lens being structured so as to form an intermediate pupil in this way, while the image forming performance of the objective lens is improved, an increase in the lens diameter of the objective lens 130 can at least be suppressed, and the total weight of the objective lens 130 due to an increase in the lens diameter can be reduced. Namely, due to the third lens group 133 being disposed so as to include the intermediate pupil position P3 at the objective lens 130, the aberration correction function that is due to the concave surface included in the third lens group 133 can be improved. Moreover, due to the concave surface being set near the intermediate pupil position, as compared with a case in which the concave surface is far from the pupil, the diverging operation at this concave surface can be strengthened more, and correction of the Petzval sum is even easier. Accordingly, the various aberrations, which arise at the second lens group that is nearest to the subject eye-side and tends to have a large lens diameter, can be easily corrected by the combining of the first lens group 134 and the third lens group 133, and excellent performance can be achieved while the UWF objective lens as a whole is compact.

By the way, in the structure of the objective lens 130, it is preferable that the distance to the conjugate position Ps of the pupil of the subject eye at which the scanning section is provided, and further, the distance to the subject eye pupil position P2 (the so-called working distances) are made to be long. On the other hand, the third lens group 133 is positioned between the first lens group 134 and the second lens group 132, and there are few constraints on the position thereof provided that the third lens group 133 is disposed so as to include the intermediate pupil position P3, and the aberration correcting ability is high. Thus, as illustrated in FIG. 3 as an example, it is preferable that the objective lens 130 that is structured so as to form an intermediate pupil be structured so as to satisfy following conditional expressions (1), given that the distance between the lens surface, which is included in the first lens group 134 and is furthest from the subject eye 12, and the position of the scanning section (the pupil conjugate position P1 that is the scanning center position Ps) (hereinafter, this distance is called the working distance at the scanning section side) is W1, and that the distance between the lens surface, which is furthest toward the subject eye 12 side at the second lens group 132, and the pupil position P2 of the subject eye (hereinafter, this distance is called the working distance at the subject eye 12 side) is W2, and that the distance between the concave surface, which is included in the third lens group 133 and has the strongest diverging power, and the intermediate pupil position P3 is D.

$$D<W1, D<W2 \qquad (1)$$

Namely, the intermediate pupil position P3, which is a pupil conjugate position that is different than the pupil conjugate position P1, is formed between the pupil conjugate position P1 at which the scanning section is disposed and the subject eye pupil P2, and the gap D, which is between the intermediate pupil position P3 and concave surface S3 that is nearest to the intermediate pupil position P3, is even smaller than the smallest value among the working distance W1 at the scanning section side and the working distance W2 at the subject eye 12 side.

By structuring the system in this way, the image forming performance of the objective lens 130 can be improved even more.

When considering the aberration of the objective lens 130, it is preferable to optimize the Petzval image surface. In this case, the Petzval curvature of the lens surface has an effect.

Thus, as illustrated as an example in FIG. 3, given that the Petzval curvature of concave surface (diverging surface) S1, which is nearest to the scanning section in the first lens group 134, is C1, and the Petzval curvature of concave surface (diverging surface) S2, which is nearest to the subject eye in the second lens group 132, is C2, and the Petzval curvature of the concave lens surface S3, which has diverging power in the third lens group 133, is C3, it is preferable that the objective lens 130 be structured so as to satisfy following conditional expressions (2).

$$C3<C1, C3<C2 \quad (2)$$

Here, the above-described Petzval curvature C is computed by following formula (3), where the radius of curvature of that surface is R, and the refractive index of the incident side of that surface N, and the refractive index of the exiting side of that surface is N'.

$$C=\{(1/N')-(1/N)\}/(-R) \quad (3)$$

Namely, the Petzval curvature C3 of the concave surface S3, which has the strongest diverging power among the concave surfaces of the lenses included in the third lens group 133, is greater negatively than whichever is greater negatively among the Petzval curvature C1 of the concave surface S1, which has diverging power and is the nearest to the scanning section among the lenses included in the first lens group 134, and the Petzval curvature C2 of the concave surface S2, which has diverging power and is the nearest to the subject eye 12 among the lenses included in the second lens group 132.

By structuring the system in this way, the image forming performance of the objective lens 130 can be improved even more. Namely, by providing the third lens group 133 that has the pupil conjugate image at the objective lens 130, the strong diverging surface S3 can be provided in a vicinity of the pupil conjugate point at this third lens group 133. Further, by structuring the Petzval curvature C3 as described above, as compared with an objective lens that does not have the third lens group 133 that has a pupil conjugate image, the Petzval sum of the objective optical system overall that includes the objective lens 130 can be made to be small, and an extremely excellent image forming performance can be achieved.

When considering the maximum aperture of the objective lens 130, the lens that is included in the second lens group 132 that is at the subject eye side has a great effect. On the other hand, in a case of forming the system such that the intermediate pupil is incorporated into the objective lens 130 by the third lens group 133, the apertures of the lenses included in the third lens group 133 are greater than the second lens group 132, and therefore, the factor that limits reduction of the maximum aperture of the objective lens 130 is the apertures of the lenses that are included in the third lens group 133, and this is an obstacle to reducing the maximum aperture of the objective lens 130.

Thus, given that the maximum effective diameter of the lenses included in the first lens group 134 is $\varphi1$, and the maximum effective diameter of the lenses include in the second lens group 132 is $\varphi2$, and the maximum effective diameter of the lenses included in the third lens group 133 is $\varphi3$, it is preferable that the objective lens 130 be structured so as to satisfy following conditional expression (4).

$$\varphi3, \varphi1 < 0.7 \cdot \varphi2 \quad (4)$$

Namely, the maximum effective diameter $\varphi1$ of the lenses included in the first lens group 134 and the maximum effective diameter $\varphi3$ of the lenses included in the third lens group 133 both are less than 70% of the maximum effective diameter $\varphi2$ of the lenses included in the second lens group 132.

By structuring the system in this way, the objective lens 130 can be made to be compact and lightweight.

In accordance with the above-described first embodiment, by structuring the objective lens 130 that satisfies the above-described conditions, the scanning center position Ps of the scanning section (the pupil conjugate position P1) is transferred to the pupil of the subject eye (the pupil position P2) by the objective lens 130. Further, at the objective lens 130, conjugate point Po of the pupil (the intermediate pupil position P3) is formed within the third lens group 133, and the conjugate point Po (the intermediate pupil position P3) is conjugate with the scanning center position Ps (the pupil conjugate position P1) as well. The concave surface (i.e., the diverging surface) at this conjugate point Po (intermediate pupil position P3) is extremely effective in aberration correction (effective in correcting the Petzval sum) of the overall objective lens 130, and the image forming performance of the objective lens 130 can be improved greatly. Further, the apertures of the first lens group 134 and the second lens group 132 can be made to be small, and the objective lens 130 overall can, although UWF, be made to be compact and lightweight.

Note that, in the first embodiment, a case is described in which light is scanned by the horizontal scanning section 142 and the vertical scanning section 148, and polygon mirrors and galvano mirrors are given as examples of the horizontal scanning section 142 and the vertical scanning section 148. However, the technique of the present disclosure is not limited to this. For example, another optical element that can scan scanning light in the Y direction may be used, and examples thereof are a MEMS (Micro-electromechanical system) mirror, a rotating mirror, a prism, and a resonant mirror.

Further, with regard to the scanning of the scanning light in the first embodiment, similar scanning can, of course, be carried out even if the X direction and the Y direction are switched.

SUITABLE EXAMPLES

Examples of the objective lens 130 of the technique of the present disclosure are described next.

Example 1

Figure 4:
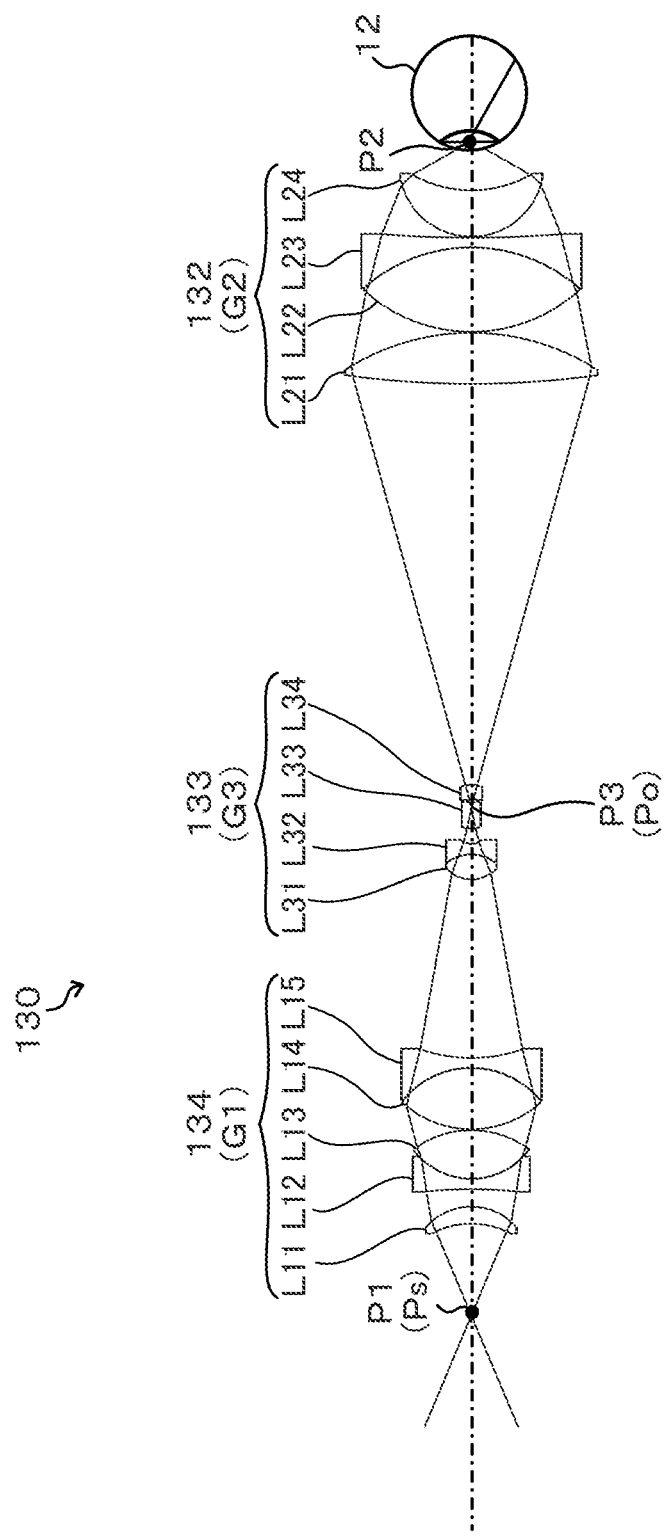
FIG. 4 is a structural drawing illustrating an example of the lens structure of an objective lens relating to Example 1.

An example of the lens structure of the objective lens 130 relating to Example 1 is illustrated in FIG. 4. The objective lens 130 is a refractive optical system that includes the lenses L11~L34.

FIG. 4 illustrates the pupil conjugate position P1 that is common to the scanning center position Ps of the scanning section, the pupil position P2 of the subject eye 12, and the intermediate pupil position P3 that is the conjugate point Po of the pupil. Note that P1, P2 and P3 in the drawing are illustrated in order to illustrate positions in the optical axis direction, and the drawing is not intended to illustrate the shapes and sizes thereof. The objective lens 130 includes, in order from the scanning section side, the first lens group 134 (G1) and the second lens group 132 (G2). Further, the third lens group 133 (G3) is disposed between the first lens group 134 (G1) and the second lens group 132 (G2). As described above, the intermediate pupil position P3 is formed within the third lens group 133 (G3) that serves as an intermediate group. The light beams illustrated in FIG. 4 are the main light beams of scanning light bundles of the maximum angle that are incident on the pupil P2 of the subject eye, and this is clear from the fact that these light beams intersect in the third lens group 133 (G3).

In the following description, there are cases in which the first lens group 134 is called first lens group G1, the second lens group 132 is called second lens group G2, and the third lens group 133 is called third lens group G3. Note that, in the example illustrated in FIG. 4, the third lens group G3 is disposed in the space that is separated by air gaps between the first lens group G1 and the second lens group G2, and, within the objective lens 130, the air gap between the third lens group G3 and the second lens group G2 is the longest air gap.

The first lens group G1 includes, in order from the pupil conjugate position P1 side that is the scanning section side toward the subject eye 12 side, the positive meniscus lens L11 whose concave surface faces the scanning section side, the negative lens L12 having a concave surface at the scanning section side, the positive lens L13, the positive lens L14 and the negative lens L15. The lens L12 and the lens L13 are cemented together, and form a lens component that is shaped as a meniscus lens whose concave surface faces the scanning section side. Further, the lens L14 and the lens L15 are cemented together, and form a lens component that is shaped as a meniscus lens whose convex surface faces the scanning section side.

The second lens group G2 includes, in order from the scanning section side toward the subject eye side, the positive lens L21, the positive lens L22, the negative lens L23 and the positive meniscus lens L24 whose convex surface faces the scanning section side. The lens L22 and the lens L23 are cemented together, and form a lens component that is shaped as a meniscus lens whose concave surface faces the subject eye 12 side.

The third lens group G3 includes, in order from the scanning section side toward the subject eye side, the positive lens 31, the negative lens L32, the meniscus lens L33 whose convex surface faces the scanning section side, and the meniscus lens L34 whose concave surface faces the scanning section side. The lens L31 and the lens L32 are cemented together, and form a lens component that is shaped as a meniscus lens. Here, the concave lens surface S3, which has the strongest diverging power of the above-described third lens group G3, is the concave surface at the subject eye side of the negative lens L33.

Lens data of Example 1 is illustrated in Table 1. The lens data illustrates, in order from the left column, the surface number (No.), the radius of curvature, the surface gap on the optical axis, the refractive index (Nd) based on the d line (wavelength 587.56 nm), and the Abbe number (vd) based on the d line. The 1st surface of the lens data is the pupil conjugate position P1 that is common to the scanning center position Ps of the scanning section, and is listed as the "aperture" of an imaginary plane (whose radius of curvature is listed as inf) in the table. The value in the final row of the surface gap column expresses the distance, on the optical axis, from the lens surface that is furthest toward the subject eye side in the table to the pupil position P2. Note that, because the objective lens 130 is an afocal system, the listings in this table assume a case in which the object is set at infinity. Further, the 7th surface, the 11th surface, the 15th surface and the 20th surface are imaginary planes for performance evaluation of the objective lens 130, and do not in any way affect that light beam that passes therethrough.

TABLE 1

| No. | radius of curvature | surface gap | Nd | vd |
|---|---|---|---|---|
| object | inf | inf | | |
| aperture | inf | 46.955 | | |
| 2 | −42.7608 | 8.707 | 1.740770 | 27.74 |
| 3 | −30.7098 | 8.932 | | |
| 4 | −224.721 | 5.304 | 1.755200 | 27.57 |
| 5 | 36.51584 | 24.840 | 1.518230 | 58.82 |
| 6 | −49.1996 | 0.500 | | |
| 7 | inf | 0.000 | | |
| 8 | 52.47307 | 31.323 | 1.744000 | 44.8 |
| 9 | −45.2337 | 5.073 | 1.698950 | 30.13 |
| 10 | 78.21317 | 25.000 | | |
| 11 | inf | 66.256 | | |
| 12 | 17.57037 | 12.698 | 1.744000 | 44.8 |
| 13 | −20.7392 | 5.447 | 1.755200 | 27.57 |
| 14 | 7.885318 | 2.866 | | |
| 15 | inf | 5.000 | | |
| 16 | 14.05853 | 13.432 | 1.755200 | 27.57 |
| 17 | 17.06274 | 1.361 | | |
| 18 | −24.7894 | 7.511 | 1.749500 | 35.25 |
| 19 | −14.3036 | 159.920 | | |
| 20 | inf | 45.000 | | |
| 21 | 474.8512 | 26.060 | 1.620410 | 60.25 |
| 22 | −118.393 | 0.500 | | |
| 23 | 81.6612 | 43.103 | 1.620410 | 60.25 |
| 24 | −83.0378 | 5.000 | 1.805180 | 25.45 |
| 25 | 573.9011 | 0.500 | | |
| 26 | 36.91632 | 23.703 | 1.744000 | 44.8 |
| 27 | 61.01281 | 25.000 | | |

Figure 5:
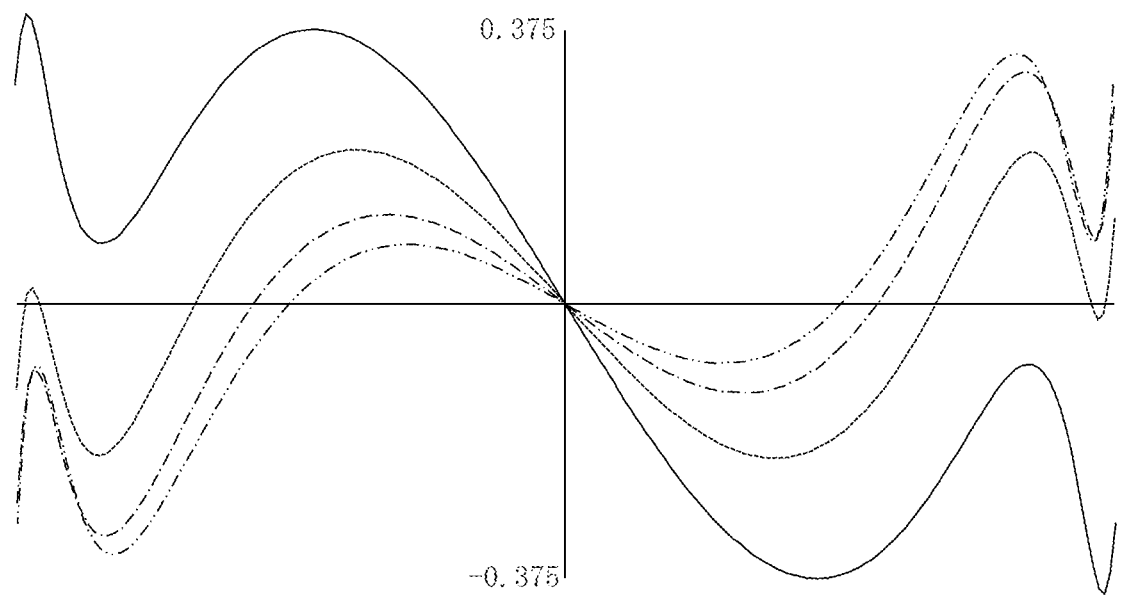
FIG. 5 is an aberration graph illustrating lateral aberration of the objective lens relating to Example 1.

FIG. 5 is a lateral aberration graph of the objective lens that is structured by the various items of Table 1. In the lateral aberration graph of FIG. 5, image height is on the vertical axis, the solid line illustrates a wavelength of 850.0 nm, the dashed line illustrates 633.0 nm, the one-dot chain line illustrates 532.0 nm, and the two-dot chain line illustrates 486.1327 nm.

As is clear from the lateral aberration graph illustrated in FIG. 5, it is confirmed that, at the objective lens 130 of Example 1, the dispersion in aberration with respect to lights of a wide wavelength region, which includes light of the visible light wavelength region and light of the near infrared region, is suppressed and is corrected well.

Example 2

Figure 6:
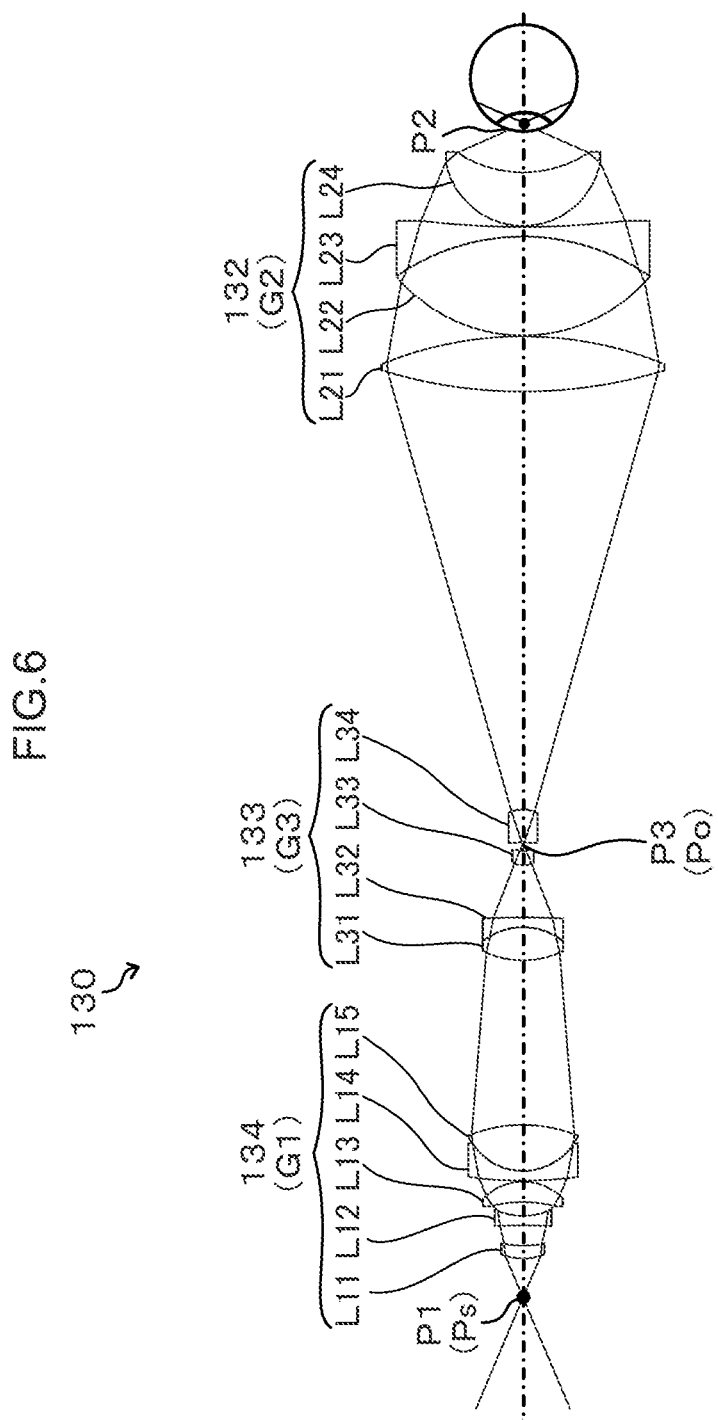
FIG. 6 is a structural drawing illustrating an example of the lens structure of an objective lens relating to Example 2.

An example of the lens structure of the objective lens 130 relating to Example 2 is illustrated in FIG. 6. Note that, because Example 2 has a structure that is similar to Example 1, the same portions are denoted by the same reference numerals, and detailed description thereof is omitted.

The first lens group G1 includes, in order from the pupil conjugate position P1 side that is the scanning section side toward the subject eye side, the positive meniscus lens L11 whose convex surface faces the scanning section side, the negative lens L12 having a concave surface at the subject eye 12 side, the positive meniscus lens L13 whose concave surface faces the scanning section side, the positive meniscus lens L14 whose convex surface faces the scanning section side, and the positive lens 15. The lens L14 and the lens L15 are cemented together, and form a lens component of a biconvex shape.

The second lens group G2 includes, in order from the scanning section side toward the subject eye side, the positive lens L21, the positive lens L22, the negative lens L23 and the positive meniscus lens L24 whose convex surface faces the scanning section side. The lens L22 and the lens L23 are cemented together, and form a lens component that is shaped as a meniscus lens whose concave surface faces the subject eye 12 side.

The third lens group G3 includes, in order from the scanning section side toward the subject eye side, the positive lens 31, the negative meniscus lens L32 whose concave surface faces the scanning section side, the lens L33 whose convex surface faces the scanning section side, and the meniscus lens L34 whose convex surface faces the subject eye 12 side. The lens L31 and the lens L32 are cemented together, and form a positive lens component. Here, the concave lens surface S3, which has the strongest diverging power of the above-described third lens group G3, is the concave surface at the subject eye side of the negative lens L33.

Lens data of Example 2 is illustrated in Table 2.

TABLE 2

| No. | radius of curvature | surface gap | Nd | vd |
|---|---|---|---|---|
| object | inf | inf | | |
| aperture | inf | 20.000 | | |
| 2 | 30.12349 | 6.632 | 1.785900 | 44.17 |
| 3 | 62.11636 | 10.184 | | |
| 4 | −335.629 | 5.000 | 1.846660 | 23.8 |
| 5 | 35.49029 | 6.949 | | |
| 6 | −69.3516 | 10.485 | 1.755000 | 52.34 |
| 7 | −27.9288 | 0.500 | | |
| 8 | 204.6868 | 5.000 | 1.698950 | 30.13 |
| 9 | 31.00309 | 23.471 | 1.755000 | 52.34 |
| 10 | −74.2074 | 30.000 | | |
| 11 | inf | 54.116 | | |
| 12 | 46.2911 | 16.902 | 1.755000 | 52.34 |
| 13 | −32.6508 | 5.000 | 1.846660 | 23.8 |
| 14 | −364.222 | 26.645 | | |
| 15 | 11.66935 | 7.439 | 1.850260 | 32.35 |
| 16 | 7.539325 | 4.349 | | |
| 17 | −14.4018 | 16.764 | 1.640000 | 60.19 |
| 18 | −15.1784 | 166.985 | | |
| 19 | inf | 46.561 | | |
| 20 | 245.4849 | 28.161 | 1.620410 | 60.25 |
| 21 | −191.188 | 0.500 | | |
| 22 | 84.21076 | 50.485 | 1.620410 | 60.25 |
| 23 | −113.415 | 5.000 | 1.846660 | 23.8 |
| 24 | 447.2304 | 0.500 | | |
| 25 | 40.128 | 27.364 | 1.754998 | 52.32 |
| 26 | 61.01281 | 25.000 | | |

Figure 7:
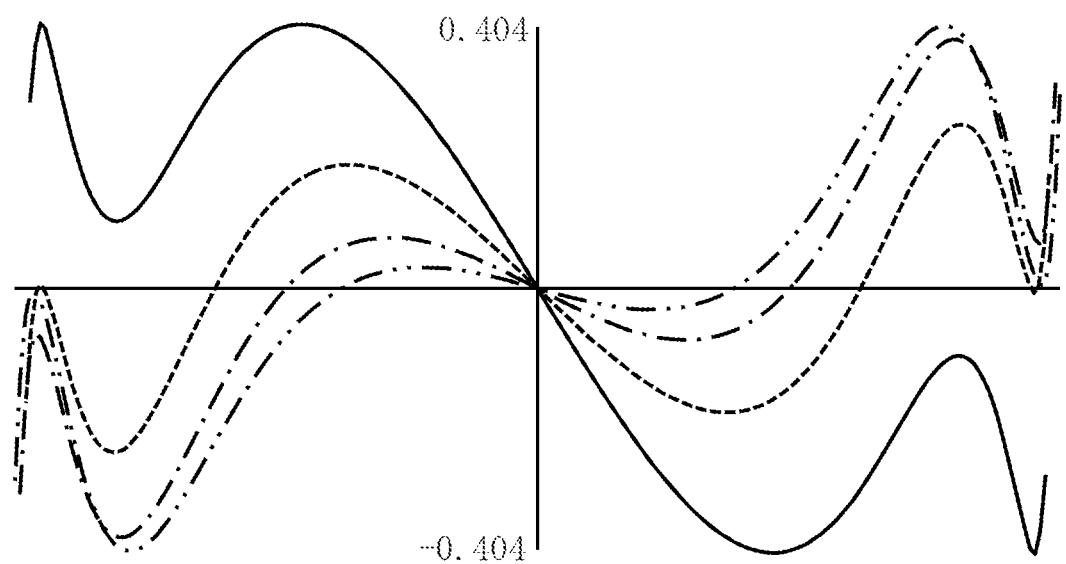
FIG. 7 is an aberration graph illustrating lateral aberration of the objective lens relating to Example 2.

FIG. 7 is a lateral aberration graph of the objective lens that is structured by the various items of Table 2.

As is clear from the lateral aberration graph illustrated in FIG. 7, it is confirmed that, at the objective lens 130 of Example 2, the dispersion in aberration with respect to lights of a wide wavelength region, which includes light of the visible light wavelength region and light of the near infrared region, is suppressed and is corrected well.

Example 3

Figure 8:
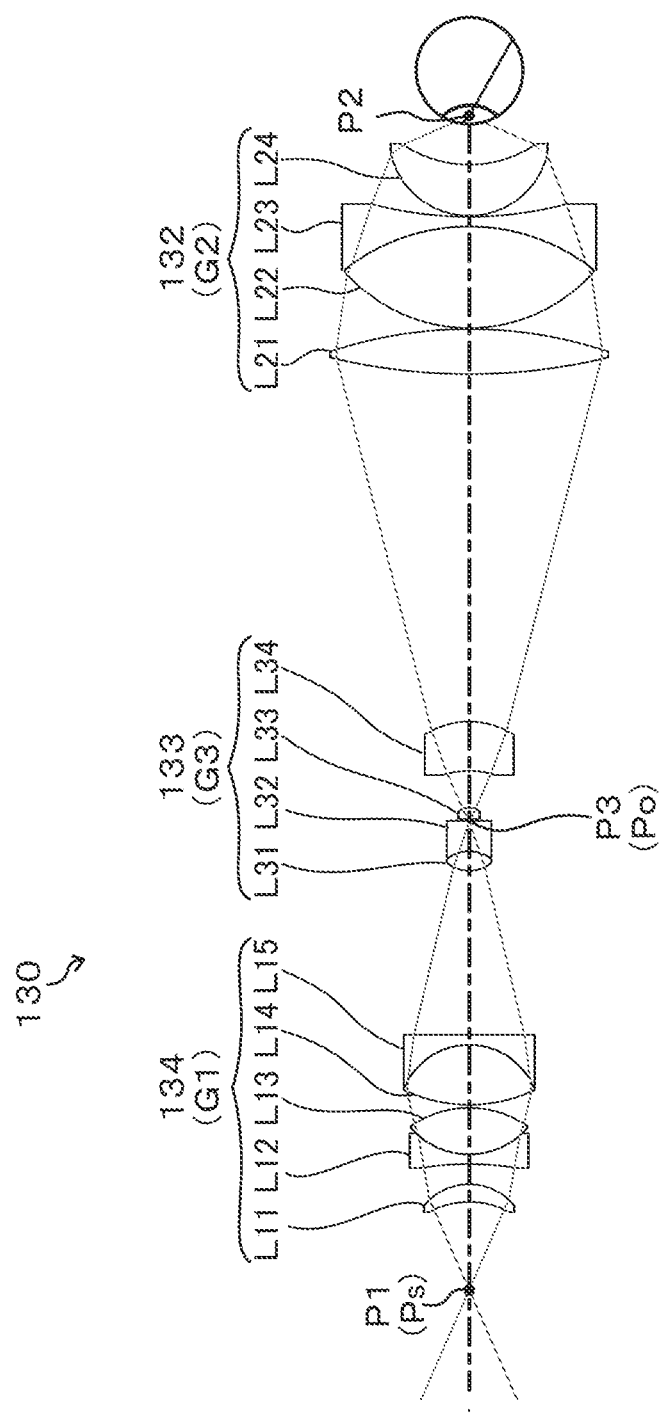
FIG. 8 is a structural drawing illustrating an example of the lens structure of an objective lens relating to Example 3.

An example of the lens structure of the objective lens 130 relating to Example 3 is illustrated in FIG. 8. Note that, because Example 3 has a structure that is similar to Example 1, the same portions are denoted by the same reference numerals, and detailed description thereof is omitted.

The first lens group G1 includes, in order from the pupil conjugate position P1 side that is the scanning section side toward the subject eye 12 side, the positive meniscus lens L11 whose concave surface faces the scanning section side, the negative lens L12, the positive lens L13, the positive lens L14, and the negative lens L15 whose concave surface faces the scanning section side. The lens L12 and the lens L13 are cemented together, and form a lens component that is shaped as a meniscus lens whose concave surface faces the scanning section side. Further, the lens L14 and the lens L15 are cemented together, and form a lens component that is shaped as a meniscus lens whose convex surface faces the scanning section side.

The second lens group G2 includes, in order from the scanning section side toward the subject eye side, the positive lens L21, the positive lens L22, the negative lens L23 and the positive meniscus lens L24 whose convex surface faces the scanning section side. The lens L22 and the lens L23 are cemented together, and form a lens component that is shaped as a meniscus lens whose convex surface faces the scanning section side.

The third lens group G3 includes, in order from the scanning section side toward the subject eye side, the positive lens 31, the negative lens L32, the meniscus lens L33 whose concave surface faces the scanning section side, and the meniscus lens L34 whose concave surface faces the scanning section side. The lens L31 and the lens L32 are cemented together, and form a lens component that is shaped as a meniscus lens whose convex surface faces the scanning section side. Here, the concave lens surface S3, which has the strongest diverging power of the above-described third lens group G3, is the concave surface at the subject eye side of the meniscus lens L33.

Lens data of Example 3 is illustrated in Table 3.

TABLE 3

| No. | radius of curvature | surface gap | Nd | Nd |
|---|---|---|---|---|
| object | inf | inf | | |
| aperture | inf | 45.000 | | |
| 2 | −42.4275 | 8.993 | 1.700000 | 48.1 |
| 3 | −29.6815 | 10.321 | | |
| 4 | −145.84 | 5.000 | 1.795040 | 28.69 |
| 5 | 39.26125 | 23.733 | 1.579570 | 53.74 |
| 6 | −51.579 | 1.575 | | |
| 7 | 77.20313 | 30.604 | 1.744000 | 44.8 |
| 8 | −35.9779 | 5.000 | 1.698950 | 30.13 |
| 9 | −36628.8 | 30.000 | | |
| 10 | inf | 54.000 | | |
| 11 | 18.21663 | 9.908 | 1.834000 | 37.18 |
| 12 | −18.5816 | 15.403 | 1.846660 | 23.8 |
| 13 | 14.15261 | 1.457 | | |
| 14 | −6.90368 | 5.526 | 1.902000 | 25.26 |
| 15 | −8.39297 | 18.701 | | |
| 16 | −44.3231 | 25.181 | 1.743200 | 49.26 |
| 17 | −41.3408 | 122.844 | | |
| 18 | inf | 54.728 | | |
| 19 | 299.3385 | 23.025 | 1.696797 | 55.53 |
| 20 | −224.23 | 0.500 | | |
| 21 | 84.28155 | 51.896 | 1.696797 | 55.53 |
| 22 | −102.322 | 5.000 | 1.846660 | 23.8 |
| 23 | 192.8745 | 0.500 | | |
| 24 | 40.93564 | 26.098 | 1.883000 | 40.66 |
| 25 | 61.01281 | 25.000 | | |

Figure 9:
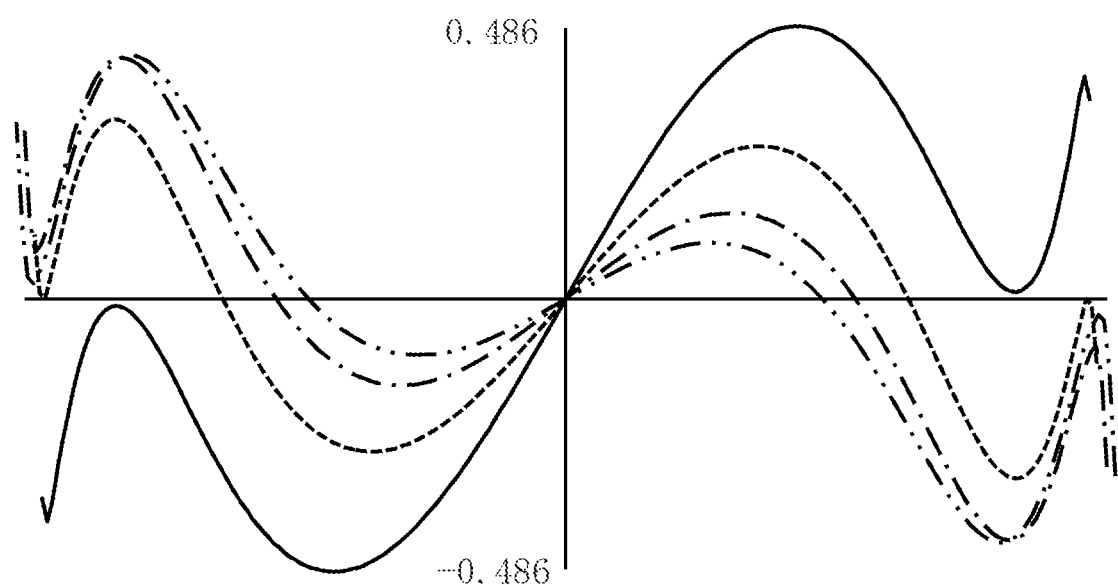
FIG. 9 is an aberration graph illustrating lateral aberration of the objective lens relating to Example 3.

FIG. 9 is a lateral aberration graph of the objective lens that is structured by the various items of Table 3.

As is clear from the lateral aberration graph illustrated in FIG. 9, it is confirmed that, at the objective lens 130 of Example 3, the dispersion in aberration with respect to lights of a wide wavelength region, which includes light of the visible light wavelength region and light of the near infrared region, is suppressed and is corrected well.

Example 4

Figure 10:
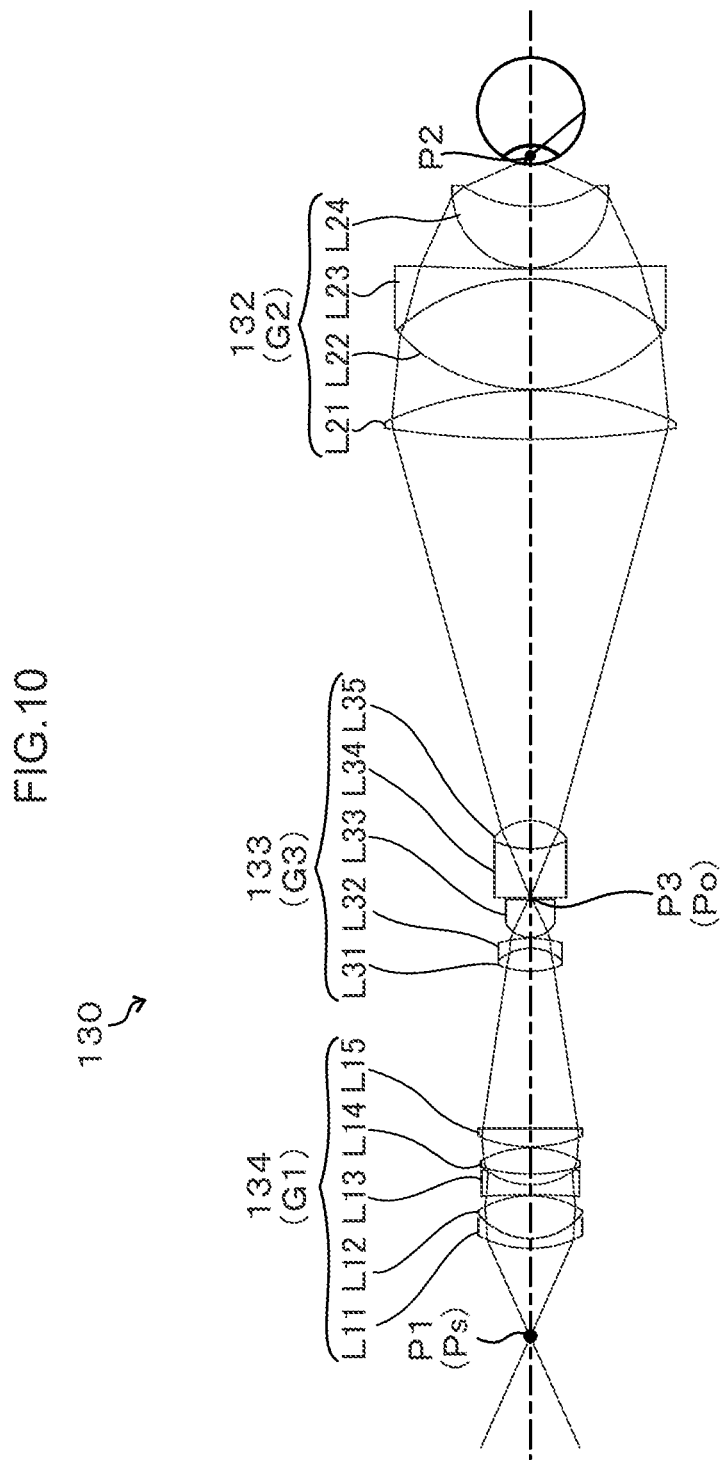
FIG. 10 is a structural drawing illustrating an example of the lens structure of an objective lens relating to Example 4.

An example of the lens structure of the objective lens 130 relating to Example 4 is illustrated in FIG. 10. Note that, because Example 4 has a structure that is similar to Example 1, the same portions are denoted by the same reference numerals, and detailed description thereof is omitted.

The first lens group G1 includes, in order from the pupil conjugate position P1 side that is the scanning section side toward the subject eye 12 side, the negative meniscus lens L11 whose convex surface faces the scanning section side, the positive lens L12, the negative lens L13, the positive lens L14 and the positive lens L15. The lens L11 and the lens L12 are cemented together, and form a positive lens component having a biconvex shape. Further, the 9th surface, which is the surface at the subject eye 12 side of the lens L15, is formed by an aspherical surface.

The second lens group G2 includes, in order from the scanning section side toward the subject eye side, the positive lens L21, the positive lens L22, the negative lens L23 and the positive meniscus lens L24 whose convex surface faces the scanning section side. The lens L22 and the lens L23 are cemented together, and form a lens component that is shaped as a meniscus lens whose convex surface faces the scanning section side.

The third lens group G3 includes, in order from the scanning section side toward the subject eye side, the positive lens 31, the negative meniscus lens L32 whose concave surface faces the scanning section side, the meniscus lens L33 whose convex surface faces the scanning section side, the negative lens 34 and the positive lens 35. The lens L31 and the lens L32 are cemented together, and form a positive lens component having a biconvex shape. The lens L34 and the lens L35 are cemented together, and form a lens component that is shaped as a meniscus lens whose concave surface faces the scanning section side. Here, the concave lens surface S3, which has the strongest diverging power of the above-described third lens group G3, is the concave surface at the subject eye side of the negative lens L33.

Lens data of Example 4 is illustrated in Table 4.

TABLE 4

| No. | | radius of curvature | surface gap | Nd | Nd |
|---|---|---|---|---|---|
| object | | 1.00E+18 | 1.00E+20 | | |
| aperture | | 1.00E+18 | 45.000 | | |
| 2 | | 56.34893 | 5.000 | 1.755200 | 27.57 |
| 3 | | 33.2776 | 21.815 | 1.622800 | 57.1 |
| 4 | | −49.7487 | 0.500 | | |
| 5 | | −386.18 | 5.000 | 1.755200 | 27.57 |
| 6 | | 36.34466 | 5.521 | | |
| 7 | | 87.77264 | 13.353 | 1.620410 | 60.25 |
| 8 | | −50.9255 | 0.548 | | |
| 9 | aspherical surface | 57.4878 | 9.271 | 1.487490 | 70.32 |
| 10 | | 1.65E+17 | 25.000 | | |
| 11 | | 1.00E+18 | 55.000 | | |
| 12 | | 42.40217 | 11.666 | 1.487490 | 70.32 |
| 13 | | −24.0717 | 5.000 | 1.755200 | 27.57 |
| 14 | | −59.5375 | 0.500 | | |
| 15 | | 14.13321 | 18.840 | 1.744000 | 44.8 |
| 16 | | 8.65902 | 1.531 | | |
| 17 | | −14.5189 | 24.664 | 1.795040 | 28.69 |
| 18 | | 43.25015 | 14.383 | 1.688930 | 31.16 |
| 19 | | −23.569 | 135.347 | | |
| 20 | | 1.00E+18 | 58.712 | | |
| 21 | | 490.9155 | 24.760 | 1.620410 | 60.25 |
| 22 | | −176.971 | 0.500 | | |
| 23 | | 92.26245 | 56.343 | | |
| 24 | | −100.651 | 5.000 | 1.755200 | 27.57 |
| 25 | | 1170.956 | 0.500 | | |
| 26 | | 39.79969 | 31.239 | 1.620410 | 60.25 |
| 27 | | 61.01281 | 25.000 | | |

At the aspherical surface listed in Table 4, given that the height in the direction orthogonal to the optical axis is h, the distance (sag amount) along the optical axis from the tangent plane at the apex of the aspherical surface to the position on the aspherical surface at height h is zs, the inverse of the radius of curvature of the near axis is c, the constant of the cone is k, the 4th-order aspherical coefficient is A, the 6th-order aspherical coefficient is B, the 8th-order aspherical coefficient is C, the 10th-order aspherical coefficient is D and the 12th-order aspherical coefficient is E, zs is expressed by the following formula.

$$zs=(c \cdot h^2)/[1+\{1-(1+k) \cdot h^2 \cdot c^2\}^{1/2}]+A \cdot h^4+B \cdot h^6+C \cdot h^8+D \cdot h^{10}+E \cdot h^{12} \ldots$$

The aspherical coefficients of the aspherical surfaces in Example 4 are listed in Table 5. In the table, the aspherical coefficients from A on are listed as the orders. "E-n" (n is an integer) in the table means "$\times 10^{-n}$".

TABLE 5

| surface 9: aspherical surface | |
|---|---|
| conic constant | 0 |
| 4th-order | −2.5207E−05 |
| 6th-order | 3.0418E−07 |
| 8th-order | −2.2241E−09 |
| 10th-order | 1.0231E−11 |
| 12th-order | −3.0965E−14 |
| 14th-order | 6.1327E−17 |
| 16th-order | −7.6047E−20 |
| 18th-order | 5.3451E−23 |
| 20th-order | −1.6247E−26 |

Figure 11:
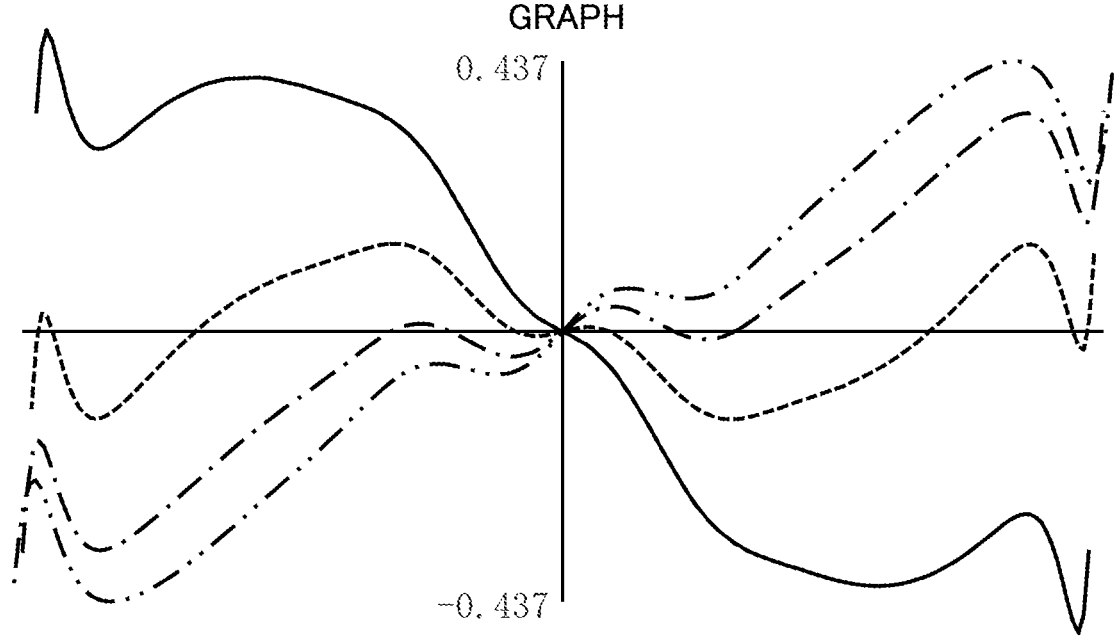
FIG. 11 is an aberration graph illustrating lateral aberration of the objective lens relating to Example 4.

FIG. 11 is a lateral aberration graph of the objective lens that is structured by the various items of Table 4 and Table 5.

As is clear from the lateral aberration graph illustrated in FIG. 11, it is confirmed that, at the objective lens 130 of Example 4, the dispersion in aberration with respect to lights of a wide wavelength region, which includes light of the visible light wavelength region and light of the near infrared region, is suppressed and is corrected well.

Next, the conformance of the above conditional expressions with the objective lenses in the respective Examples of above-described Example 1 through Example 4 is described. Values relating to the above conditional expressions for Example 1 through Example 4 respectively are listed in Table 6.

TABLE 6

| | Example 1 | Example 2 | Example 3 | Example 4 |
|---|---|---|---|---|
| D (surface no.) | 13.82 (14) | 3.31 (16) | 1.93 (14) | 5.26 (16) |
| W1 | 46.95 | 20.00 | 45.00 | 45.00 |
| W2 | 25.00 | 25.00 | 25.00 | 25.00 |
| C1 | −0.00995 | 0.0146 | −0.00971 | 0.00764 |
| C2 | −0.00699 | −0.00705 | −0.00769 | −0.00628 |
| C3 | −0.05457 | −0.061 | −0.0687 | −0.0493 |
| φ1 | 68 | 53 | 65 | 49 |
| φ2 | 125 | 140 | 134 | 144 |
| φ3 | 24 | 39 | 43 | 35 |
| M | 2.1 | 2.1 | 2.2 | 2.1 |
| f3 | 64.01 | 73.56 | 61.92 | 63.13 |

As is clear from Table 6, it is clear that the objective lenses of Example 1 through Example 4 are in conformance with the above conditional expressions.

Second Embodiment

A second embodiment is described next. In the second embodiment, the objective lens 130, which is the main portion of the imaging optical system 116A relating to the first embodiment, is formed as an attached optical system, and can be attached to and removed from a portable terminal that has an imaging function. Because the structure of the second embodiment is substantially similar to the first embodiment, the same portions are denoted by the same reference numerals, and description thereof is omitted, and mainly the portions that are different are described.

Figure 12:
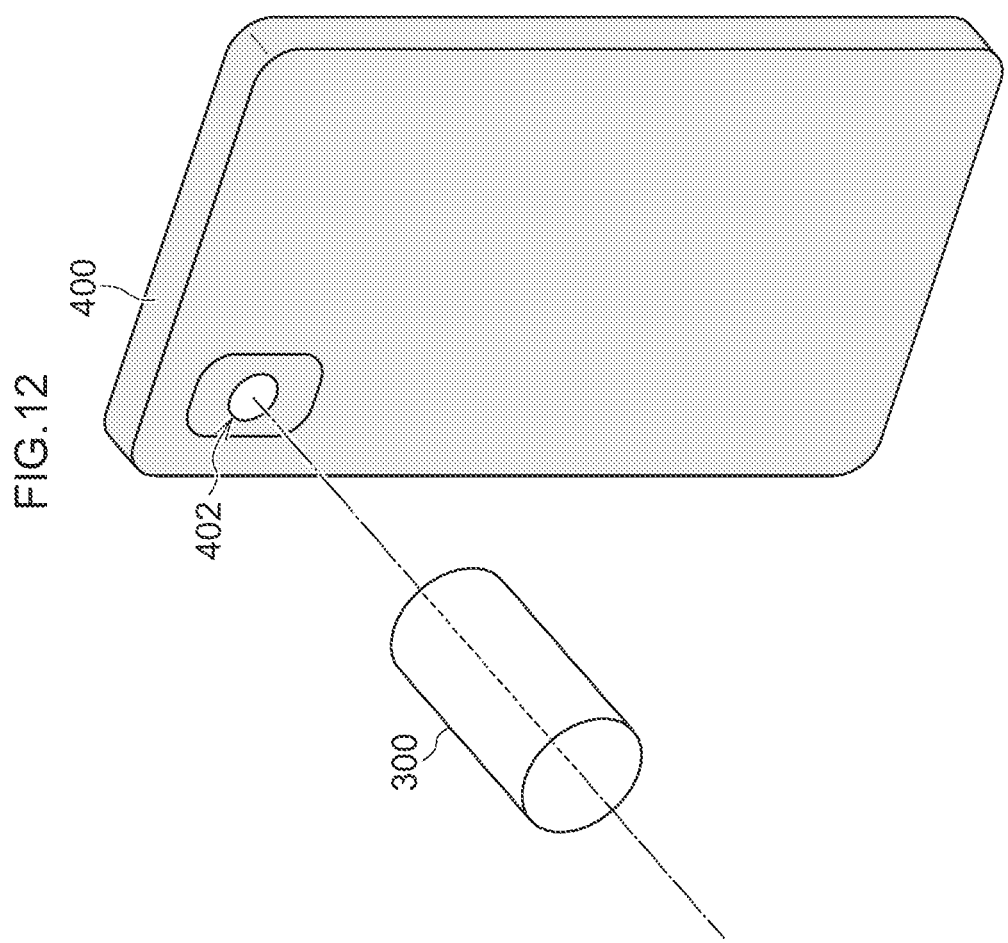
FIG. 12 is a schematic structural drawing illustrating a structure in which an attached optical system relating to a second embodiment is made to be attachable to and removable from a portable terminal.

FIG. 12 illustrates an example of a structure in which an attached optical system 300 relating to the second embodiment can be attached to and removed from a portable terminal 400 that has an imaging function.

As illustrated in FIG. 12, the portable terminal 400 has an imaging section 402 for realizing the imaging function. The imaging section 402 operates in a usual imaging mode, in which the imaging section 402 captures an image of a subject at infinity such as a landscape or the like, by user operation of an unillustrated operation portion that the portable terminal 400 has. Namely, the imaging section 402 of the portable terminal 400 has a lens 404 for a portable terminal (FIG. 13), and is structured so as to, by operation in the usual imaging mode, form an image on an imaging element 406 (FIG. 13) when parallel light is incident.

Figure 13:
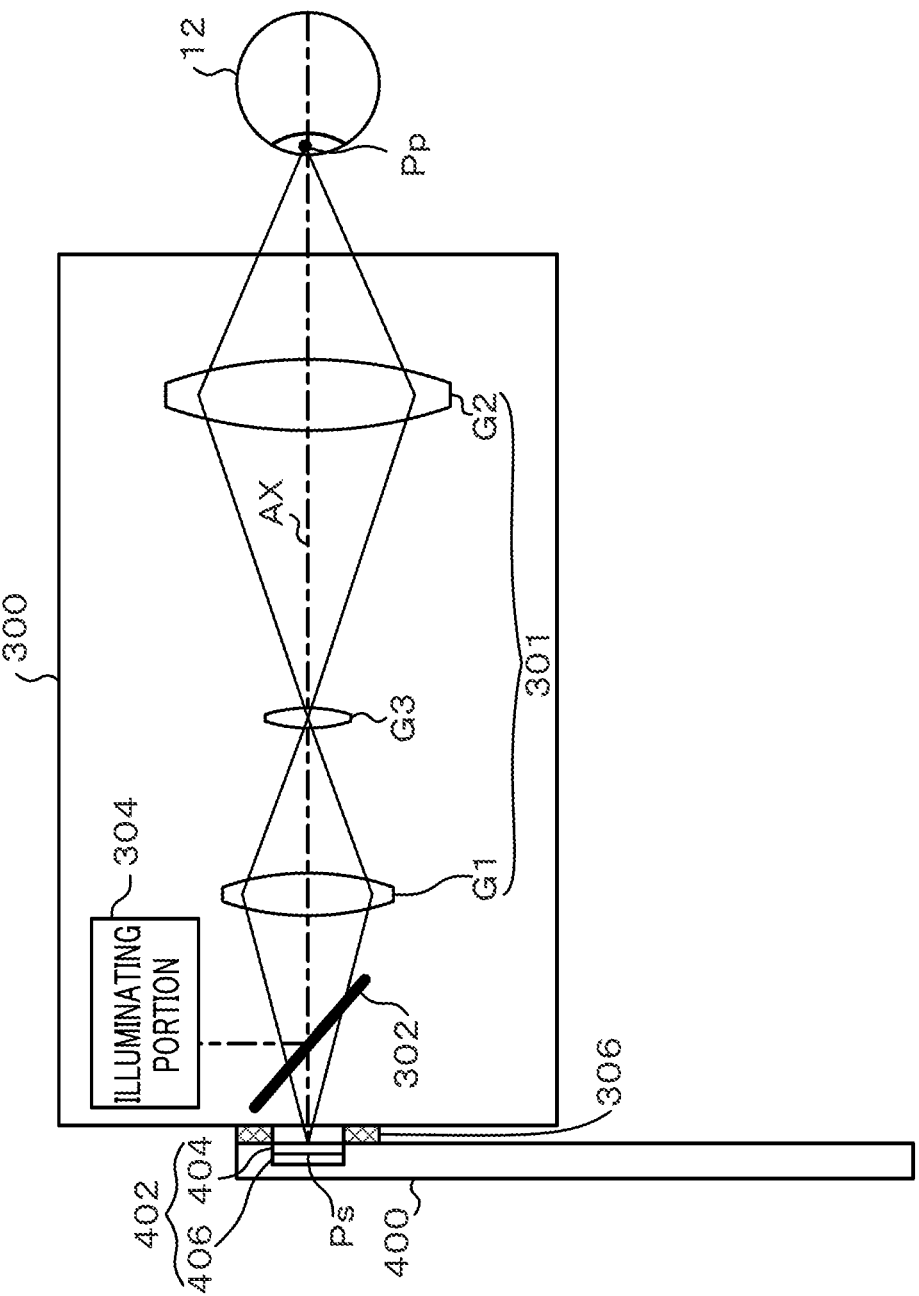
FIG. 13 is a schematic structural drawing illustrating an example of the structure of the attached optical system relating to the second embodiment.

FIG. 13 illustrates an example of the structure of the attached optical system 300 relating to the second embodiment. A state in which the attached optical system 300 is attached to the portable terminal 400 is illustrated in FIG. 13. The attached optical system 300 has the first lens group G1, the second lens group G2 and the third lens group G3 that structure the above-described objective lens 130. Because the structures and functions of these respective lens groups are similar to the first embodiment, detailed description thereof is omitted.

At the attached optical system 300 relating to the second embodiment, the point that an illuminating portion 304 that emits illumination light, and a half mirror 302 that guides the illumination light that is from the illuminating portion to the optical path that runs along the optical axis AX, are provided at the objective lens 130 relating to the first embodiment, is different. The illuminating portion 304 emits the illumination light that illuminates the subject eye 12. The half mirror 302 guides the illumination light that is from the illuminating portion 304 to the optical path that runs along the optical axis AX.

Note that, in a case in which the portable terminal 400 has a subject illuminating portion that illuminates the subject, it suffices for the attached optical system 300 to, instead of the illuminating portion 304 and the half mirror 302, employ the illumination light that is emitted from the subject illuminating portion, and have an optical system that guides the illumination light that is from the subject illuminating portion to the optical path that runs along the optical axis AX. Further, the illuminating portion 304 may be an independent structure, and not be provided at the attached optical system 300.

The attached optical system 300 has an attaching portion 306 that attaches the attached optical system 300 to the portable terminal 400, in order to form a structure in which the attached optical system 300 and the portable terminal 400 can be attached and removed. Due to the attached optical system 300 having this attaching portion 306, a structure in which the attached optical system 300 can be attached to and removed from the portable terminal 400 becomes possible.

The first lens group G1 and the second lens group G2 that are included in the attached optical system 300 function as an objective optical system 301 that forms a pupil that has a conjugate relationship with the pupil of the subject eye 12. The attached optical system 300 and the portable terminal 400 are fixed by the attaching portion 306 such that the incident pupil of the imaging section 402 of the portable terminal 400 is positioned at the position (the pupil conjugate position P1) of the pupil that is in a conjugate relationship with the pupil of the subject eye 12 formed by the objective optical system 301.

By structuring the system in this way, a fundus image of the subject eye 12 can be imaged by the simple structure of merely attaching the attached optical system 300 to the portable terminal 400.

Third Embodiment

A third embodiment is described next.

In the first embodiment, the imaging optical system 116A, which functions as a posterior eye portion observing optical system that observes the posterior eye portion of the subject eye 12, is mainly described. The third embodiment is formed so as to be able to switch so as to function as an anterior eye portion observing optical system that observes the anterior eye portion of the subject eye 12, by inserting an optical module for anterior eye portion observation into the imaging optical system 116A that functions as the posterior eye portion observing optical system relating to the first embodiment. Because the structure of the third embodiment is substantially similar to the first embodiment, the same portions are denoted by the same reference numerals, and description thereof is omitted, and the portions that differ are mainly described.

Figure 14:
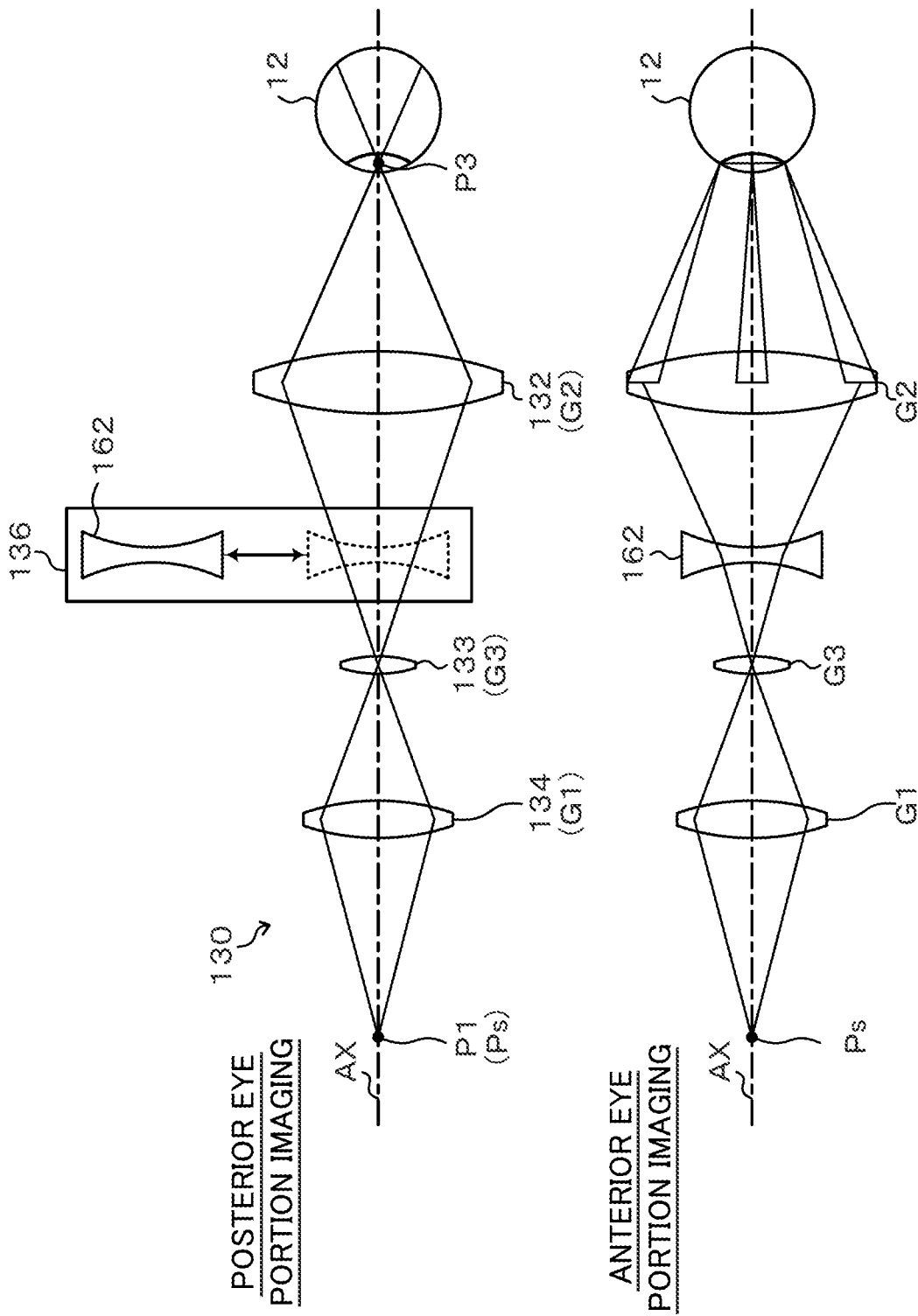
FIG. 14 is a schematic structure drawing of an objective lens that structures an imaging optical system of a third embodiment.

FIG. 14 illustrates an example of the structure of the objective lens 130 at the imaging optical system 116A relating to the third embodiment. The imaging optical system 116A relating to the third embodiment has the objective lens 130 that can switch between a posterior eye portion observing optical system and an anterior eye portion observing optical system. The objective lens 130 has, in order from the scanning section (e.g., the horizontal scanning section 142) side, the first lens group 134 and the second lens group 132, and has the third lens group 133 in the space between the first lens group 134 and the second lens group 132. The structures of these first lens group 134 (G1), second lens group 132 (G2) and third lens group 133 (G3) are similar to the first embodiment, and therefore, detailed description thereof is omitted.

The imaging optical system 116A has an optical module 136 for anterior eye portion observation that can be inserted onto and removed from the optical path of the objective lens 130. Due to the optical module for anterior eye portion observation being placed on the optical path of the objective lens 130, the imaging optical system 116 can switch from an optical system for posterior eye portion observation to an optical system for anterior eye portion observation. Specifically, as illustrated in FIG. 14, the optical module 136 for anterior eye portion observation is inserted onto the optical path of the objective lens 130, e.g., on the optical path between the first lens group 134 (G1) that has positive refractive power and the second lens group 132 (G2) that has positive refractive power, which structure the objective lens 130. Preferably, as illustrated in FIG. 14, the optical module 136 for anterior eye portion observation is inserted between the second lens group 132 (G2) and the third lens group 133 (G3).

The optical module 136 has, at the interior thereof, an optical element including a lens 162 that serves as a switching lens and has negative power. When the lens 162 is placed on the optical axis of the objective lens 130, the lens 162 operates as a switching lens for switching a posterior eye portion observing optical system 300 to an anterior eye portion observing optical system 400. In a case in which the lens 162 is inserted on the optical path of the objective lens 130, the scanning position (the scanning center position Ps) of the scanning section (e.g., the horizontal scanning section 142) and the pupil position P3 of the subject eye 12 are not conjugate, and the parallel light from the scan position of the scanning section is collected at the anterior eye portion. The diameter of the light bundle that passes through the lens 162 is smaller than the diameters of the light bundles that pass through the first lens group 134 and the second lens group 132, respectively. Accordingly, the effective diameter of the lens 162 is small as compared with the effective diameters of the lens groups that structure the objective lens 130. Therefore, the optical module 136 can be structured to be compact. Note that the optical element is not limited to the lens 162 that has negative power, and, instead of the lens 162, an optical member such as, for example, a Fresnel lens, a DOE (Diffractive Optical Element) or the like may be used.

More specifically, the imaging optical system 116A is a structure in which the optical module 136 for anterior eye portion observation can be inserted onto and removed from the optical path of the objective lens 130, which is the optical path of an observing optical system for posterior eye portion observation, either manually by an operator (e.g., an ophthalmologist) or automatically. In a case in which the optical module 136 is not disposed on the optical path of the objective lens 130, a posterior eye portion observing optical system is structured as the observing optical system, and the ophthalmic device 110 acquires an image of the posterior eye portion of the subject eye 12 thereby. On the other hand, in a case in which the optical module 136 is inserted on the optical path of the objective lens 130, an anterior eye portion observing optical system is structured as the observing optical system, and the ophthalmic device 110 acquires an image of the anterior eye portion of the subject eye 12 thereby.

Note that the optical module 136 for anterior eye portion observation may have an eye tracking module that tracks the sightline direction and is used at the time of anterior eye portion observation, a fixation lamp that guides the sightline direction of the subject eye 12, a camera, and an illumination device.

As described above, in accordance with the third embodiment, by inserting and removing the optical module 136 for anterior eye portion observation onto and from the optical path of the objective lens 130 that functions as an observing optical system for posterior eye portion observation, the imaging optical system 116A can be instantaneously switched between an anterior eye portion observing optical system that observes the anterior eye portion of the subject eye 12 and a posterior eye portion observing optical system that observes the posterior eye portion.

Suitable Example

An Example of the objective lens 130 relating to the third embodiment is described next.

Example 5

Figure 15:
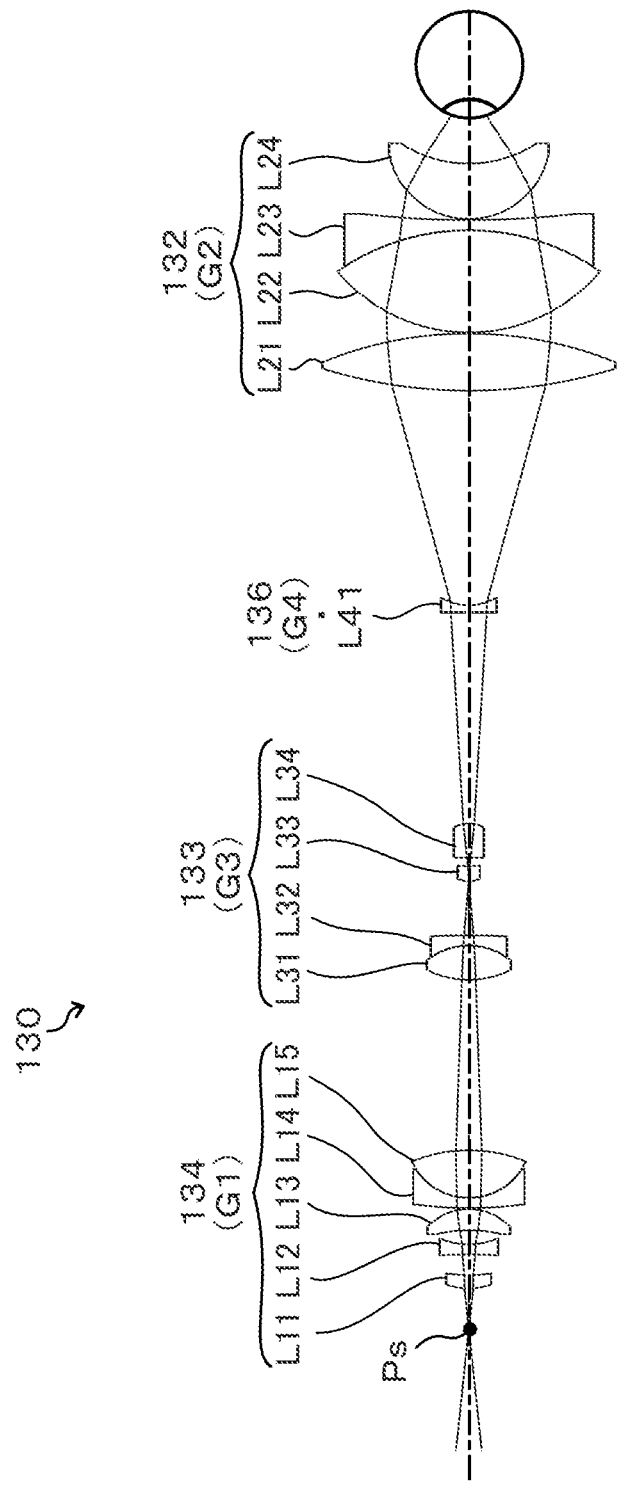
FIG. 15 is a structural drawing illustrating an example of the lens structure of an objective lens relating to Example 5.

FIG. 15 illustrates an example of the lens structure of the objective lens 130 relating to Example 5. Note that, because Example 5 has a structure that is similar to Example 2, the same portions are denoted by the same reference numerals, and detailed description thereof is omitted. In Example 5, the point that the lens 136 that is included in the optical module 136 for anterior eye portion observation is added between the second lens group 132 and the third lens group 133 in the structure of Example 2, is different.

In Example 5, a negative lens L41 is disposed between the second lens group G2 and the third lens group 133, and specifically, between the positive lens L21 and the negative lens L34.

Lens data of Example 5 is illustrated in Table 7.

TABLE 7

|  | radius of curvature | surface gap | Nd | Nd |
|---|---|---|---|---|
| object | inf | inf |  |  |
| aperture | inf | 20.000 |  |  |
| 2 | 30.12349 | 6.632 | 1.785900 | 44.17 |
| 3 | 62.11636 | 10.184 |  |  |
| 4 | −335.629 | 5.000 | 1.846660 | 23.8 |
| 5 | 35.49029 | 6.949 |  |  |
| 6 | −69.3516 | 10.485 | 1.755000 | 52.34 |
| 7 | −27.9288 | 0.500 |  |  |
| 8 | 204.6868 | 5.000 | 1.698950 | 30.13 |
| 9 | 31.00309 | 23.471 | 1.755000 | 52.34 |
| 10 | −74.2074 | 30.000 |  |  |
| 11 | inf | 54.116 |  |  |
| 12 | 46.2911 | 16.902 | 1.755000 | 52.34 |
| 13 | −32.6508 | 5.000 | 1.846660 | 23.8 |
| 14 | −364.222 | 26.645 |  |  |
| 15 | 11.66935 | 7.439 | 1.850260. | 32.35 |
| 16 | 7.539325 | 4.349 |  |  |
| 17 | −14.4018 | 16.764 | 1.640000 | 60.19 |
| 18 | −15.1784 | 104.193 |  |  |
| 19 | inf | 3.500 | 1.516800 | 63.8807 |
| 20 | −25.7000 | 105.853 |  |  |
| 21 | 245.4849 | 28.161 | 1.620410 | 60.25 |
| 22 | −191.188 | 0.500 |  |  |
| 23 | 84.21076 | 50.485 | 1.620410 | 60.25 |
| 24 | −113.415 | 5.000 | 1.846660 | 23.8 |
| 25 | 447.2304 | 0.500 |  |  |
| 26 | 40.128 | 27.364 | 1.754998 | 52.32 |
| 26 | 61.01281 | 25.000 |  |  |

Although not illustrated, at the objective lens 130 of Example 5, even in a case in which the optical module 136 for anterior eye portion observation is inserted on the optical path of the objective lens 130 that functions as an observing optical system for posterior eye portion observation, aberration with respect to lights of the wavelength region for anterior eye portion imaging (the visible light wavelength region or the near infrared region) is corrected well.

Fourth Embodiment

A fourth embodiment is described next. Because the structure of the fourth embodiment is substantially similar to the above-described embodiments, the same portions are denoted by the same reference numerals, and description thereof is omitted.

In the above-described embodiments, the objective lens 130, which is included in the imaging optical system 116A for observing the subject eye 12, can suppress the dispersion in aberration with respect to lights of a wide wavelength region, which includes light of the visible light wavelength region and light of the near infrared region. Accordingly, the objective lens 130 relating to the above-described respective embodiments can be applied to ophthalmic devices that are exclusively used for SLO and OCT, respectively. In addition, in a combined device that has both functions of SLO and OCT, the objective lens 130 can be used as an objective lens shared by SLO and OCT (can be used for both). In the fourth embodiment, the objective lens 130 is used in common for SLO and OCT.

Because the wavelengths of the lights that are used are different in an optical system for SLO and an optical system for OCT, it is preferable to adjust the lens structures to as to accord with them respectively. Thus, in the fourth embodiment, because the objective lens 130 is used in common, the objective lens is structured by two lens groups, and the objective lens for SLO is made to be the reference, and the difference between the optical system for SLO and the optical system for OCT is absorbed by one lens group (e.g., the first lens group G1). Specifically, by structing the objective lens by two lens groups, and using the front lens group (the second lens group G2) in common, and changing the structure of the rear lens group (the first lens group G1), the system is structured so as to switch from functioning as a relay lens device for SLO to functioning as a relay lens device for OCT.

FIG. 16 illustrates an example of the structure of the objective lens 130 in the imaging optical system 116A relating to the fourth embodiment.

As illustrated in FIG. 16, at the objective lens 130 relating to the fourth embodiment, a region that propagates substantially parallel light is formed on the optical path, and a splitting/combining element (e.g., a dichroic mirror) DM1, which splits and combines the optical path at the formed region, is provided. In the example illustrated in FIG. 16, an optical system is formed at a parallel system between the first lens group G1 and the third lens group G3. In this case, the first lens group G1 is a lens group such that the light, which heads from the first lens group G1 toward the third lens group G3, becomes a parallel system.

Further, the third lens group G3 is a lens group such that the light of the parallel system from the first lens group G1 includes the intermediate pupil position P3. Specifically, the third lens group G3 includes, in order from the scanning section side, a lens group G31, a lens group G32 and a lens group G33. The lens group G31 is a lens group having the function of forming an intermediate pupil at the interior of the third lens group G3, from the light of the parallel system from the first lens group G1. The lens group G32 is a lens group having a concave surface at the intermediate pupil position P3 or in a vicinity thereof. The lens group G33 is a lens group having the function of transferring the intermediate pupil toward the second lens group.

For example, the optical path that includes the optical axis AX illustrated in FIG. 16 is used as the SLO optical path, and the splitting/combining element DM1 is disposed at a region between the first lens group G1 and the third lens group G3, and is used at the OCT optical path. By doing so, the two optical systems of SLO and OCT can be combined.

In this way, in the fourth embodiment, by forming a region, which propagates substantially parallel light, on the optical path of the objective lens 130, and disposing the splitting/combining element DM1, which splits the optical path, at the formed region, the two optical paths of SLO and OCT can be combined.

The fourth embodiment describes a case of using an OCT optical path formed by a dichroic mirror or the like at a region that propagates substantially parallel light. However, the region that propagates substantially parallel light is not limited to a region between the first lens group G1 and the third lens group G3. For example, a splitting/combining element may be provided in any space between the first lens group G1 and the third lens group G3 of the objective lenses 130 relating to the above-described respective embodiments. Further, although the fourth embodiment describes a case in which the splitting/combining element DM1 is disposed at a region that propagates substantially parallel light, the fourth embodiment is not limited to this. For example, a splitting/combining element DM2 may be disposed at a region between the lens group G31 and the lens group G32 at the third lens group G3, or a splitting/combining element DM3 may be disposed at a region between the lens group G32 and the lens group G33, or a splitting/combining element DM4 may be disposed at a region between the third lens group G3 and the second lens group G2.

In the structure illustrated in FIG. 16, of course, the optical path that includes the optical axis AX may be used as the OCT optical path, and the splitting/combining element DM1 may be placed and used at the SLO optical path.

Note that, when an optical element (the splitting/combining element DM4) is placed between the second lens group G2 and the third lens group G3, there are cases in which flares arise in the visible light region. Therefore, in a case in which an optical element (the splitting/combining element DM4) is placed between the second lens group G2 and the third lens group G3, and the optical path is split, it is preferable to use a splitting optical path as the OCT optical path.

In this way, in accordance with the fourth embodiment, the objective lens 130 can be used also as a combined device that has the functions of both SLO and OCT.

Fifth Embodiment

A fifth embodiment is described next. Because the structure of the fifth embodiment is substantially similar to the fourth embodiment, the same portions are denoted by the same reference numerals, and description thereof is omitted.

There are cases in which an ophthalmic device has both a fixation target projecting optical system that provides a fixation target by a fixation lamp, and an subject eye position imaging optical system that captures an image of the position of the subject eye 12 by a camera or the like. At these observing optical systems such as the fixation target projecting optical system and the subject eye position imaging optical system or the like, the image forming performance is sufficient mainly by appropriately carrying out correction with respect to the visible region. On the other hand, at the objective lens 130 of the present disclosure, correction of aberration in a wide wavelength region that includes both the visible region for SLO and the near infrared region for OCT is extremely good. In this case, the system can be structured such that aberration correction in mainly the visible region is carried out at further toward the subject eye 12 side than the pupil conjugate position P3 in the objective lens 130, and aberration correction in the near infrared region is carried out by an optical system that is further toward the scanning system side than the pupil conjugate position P3. Namely, for the aberration correction, the wavelength region is divided into plural regions, and aberration correction for the different wavelength regions can be carried out respectively thereat. For example, the second lens group G2 is used as the optical system that is further toward the subject eye 12 side than the intermediate pupil conjugate position P3, and the first lens group G1 is used as the optical system that is further toward the scanning section side than the intermediate pupil conjugate position P3. Further, in a case of combining the optical paths of the observing optical systems such as the fixation target projecting optical system and the subject eye position imaging optical system and the like, a prism for optical path combining can be disposed within the third lens group G3 at a region before or after the pupil conjugate position P3 (the region where the splitting/combining element DM2 or DM3 illustrated in FIG. 16 is disposed). In a case of giving more consideration to the effects of aberration in the visible region, it is preferable to place the prism for optical path combining, which combines the optical paths, at the region where the splitting/combining element DM3 is disposed. Further, in a case of using infrared light in the subject eye position imaging optical system, it is effective to provide the prism for optical path combining at the position of DM1 that is at the scanning section side in FIG. 16. In either case, in a case of providing a prism for optical path combining between the subject eye pupil P2 and the pupil conjugate position P1 at which the scanning section is disposed, it is important to adjust the balance of the aberration correcting functions at the respective groups of the objective lens that is structured to include three groups.

In this way, in accordance with the fifth embodiment, observing optical systems such as the fixation target projecting optical system and the subject eye position imaging optical system and the like can be provided at the ophthalmic device 110 by a simple structure.

Sixth Embodiment

A sixth embodiment is described next. Because the structure of the sixth embodiment is substantially similar to the above-described embodiments, the same portions are denoted by the same reference numerals, and description thereof is omitted.

In the above-described embodiments, the objective lens 130, which is included in the imaging optical system 116A for observing the subject eye 12, can suppress dispersion in aberration with respect to lights of a wide wavelength region including light of the visible light wavelength region and light of the near infrared region. Accordingly, the objective lens 130 relating to the above-described respective embodiments can be applied an ophthalmic device that is exclusively used for SLO, and the ophthalmic device that is exclusively used for SLO can be switched from an ophthalmic device for SLO to use as an ophthalmic device for OCT. The sixth embodiment is structured such that an ophthalmic device that is exclusively used for SLO can be switched from an ophthalmic device for SLO to an ophthalmic device for OCT.

FIG. 17 illustrates an example of the structure of an ophthalmic device 110A relating to the sixth embodiment.

As illustrated in FIG. 17, the ophthalmic device 110A relating to the sixth embodiment has the relay lens device 140 that is exclusively used for SLO and that relays the scanning light of the SLO unit, and the objective lens 130 (refer to FIG. 2 as well), and is formed as a device that is exclusively used for SLO. The relay lens device 140 is disposed at a relay unit 140A that can be inserted into and removed from the ophthalmic device 110A. Namely, the ophthalmic device 110A functions as a device that is exclusively used for SLO, due to the relay unit 140A being mounted to a relay lens mounting portion (not illustrated) of the ophthalmic device 110A.

On the other hand, a relay unit 140B can be mounted to the relay lens mounting portion (not illustrated) of the ophthalmic device 110A. A dichroic mirror DM5 that splits and combines light is disposed on the optical path of the relay lens device 140 at the relay unit 140B. Further, an OCT unit is disposed at the relay unit 140B on the optical path that has been split-off by the dichroic mirror DM5. Accordingly, by mounting the relay unit 140B to the relay lens mounting portion (not illustrated) of the ophthalmic device 110A, the ophthalmic device 110A functions as a SLO device and can also function as an OCT device.

In this way, in accordance with the sixth embodiment, there is an ophthalmic device that can work as both a SLO device and an OCT device by replacing the relay lens device 140, which a device that is exclusively used for SLO, with a relay lens 141 that has the same components as the relay lens device 140 and has the dichroic mirror DM5 built therein, and by mounting the OCT unit.

Further, a great decrease in cost is possible by using the objective lens 130 in common, and using the lens structures of the relay lens device 140 and the relay lens 141 in common, and structuring the ophthalmic device in which both SLO and OCT are possible from a device that is exclusively used for SLO.

Note that, although the above describes a case in which the relay unit is mounted to the relay lens mounting portion (not illustrated), there may be a structure in which the relay lens device 140 is formed by plural lens groups, and the relay lens device 140 is fixed to the ophthalmic device 110A, and the dichroic mirror DM5 is inserted into and removed from the space between adjacent lens groups. In this case, the costs can be further decreased because switching of the relay lens device 140 is unnecessary.

In this way, because the technique of the present disclosure includes the function of structuring an ophthalmic device at which both SLO and OCT are possible from an ophthalmic device that functions as a device used exclusively for SLO, the technique of the present disclosure includes the following first technique.

(First Technique)

An ophthalmic device having:
  a first optical path having a scanning section for angle-scanning a light bundle that is from a first light source;
  an objective lens guiding the light bundle scanned by the scanning section to an subject eye; and
  a relay lens disposed between the scanning section and the objective lens, and guiding the scanning light bundle that is from the scanning section to the objective lens,
  wherein the relay lens has two lens groups, and includes an optical element for optical path combining/splitting that can be inserted and removed from between the two lens group, and a second optical path, which guides a light bundle, which is from a second light source different from the first light source, to the objective lens, is structured on a reflection optical path of the optical element for optical path combining/splitting in a state in which the optical element for optical path combining/splitting is disposed on the optical path.

Note that the dichroic mirror D5 is an example of the optical element for optical path combining/splitting of the above-described first technique.

Further, because the optical system of the first technique includes an aberration correcting technique, following supplemental technique 1 and supplemental technique 2 are included.

(Supplemental Technique 1 of First Technique)

The ophthalmic device of the first technique, wherein, in a first combined optical system that includes the relay lens and the objective lens, first aberration correction is carried out on the light bundle from the first light source, and, at a second combined optical system that includes the objective lens and the lens group that is at the objective lens side among the two lens groups that structure the relay lens, second aberration correction that is different than the first aberration correction is carried out on the light bundle from the second light source.

(Supplemental Technique 2 of First Technique)

The ophthalmic device of the first technique, wherein the objective lens is a lens component that shared by the relay lens of the first optical path and the relay lens of the second optical path, and at which aberration correction is carried out on the light bundle from the first light source and the light bundle from the second light source.

Seventh Embodiment

A seventh embodiment is described next. Because the structure of the seventh embodiment is substantially similar to the above-described embodiments, the same portions are denoted by the same reference numerals, and description thereof is omitted.

In the technique of the present disclosure, the ophthalmic device includes at least one structure among respective optical systems that are an optical system for SLO that uses light mainly of a wavelength in the visible region, an optical system for OCT that uses light mainly of a wavelength in the near infrared region, and an alignment optical system that is used in alignment of the subject eye. Note that the alignment optical system includes a fixation target projecting optical system and an subject eye position imaging optical system. At these respective optical systems, there are cases in which the aberration correction with respect to the lens system is different at the SLO optical system and the OCT optical system. Thus, the seventh embodiment describes structural examples of ophthalmic devices that take aberration correction at the objective lens into consideration.

First Structural Example

An ophthalmic device that serves as a first structural example is an ophthalmic device for SLO that has an objective lens at which chromatic aberration correction in at least the visible region is carried out. An optical system, which includes an objective lens at which this chromatic aberration correction in the visible region is carried out, is described.

FIG. 18 illustrates an example of the structure of an imaging optical system 116B in an ophthalmic device relating to the first structural example.

As illustrated in FIG. 18, the ophthalmic device relating to the first structural example functions as a device used exclusively for SLO. Specifically, the imaging optical system 116B has, in order from the subject eye 12 side, an objective lens 1130 at which chromatic aberration correction in the visible region is carried out, the horizontal scanning section (also indicated as H scanner in FIG. 18) 142, the relay lens device 140, and the vertical scanning section (also indicated as V scanner in FIG. 18) 120 such as a polygon mirror or the like.

The horizontal scanning section 142 is an optical scanner that scans, in the horizontal direction, the SLO laser light that is incident via the relay lens device 140. The vertical scanning section 120 is an optical scanner that scans, in the vertical direction, the laser light that is incident from the SLO unit 18. In the present embodiment, a galvano mirror is used as an example of the horizontal scanning section 142, and further, a polygon mirror is used as an example of the vertical scanning section 120.

The relay lens device 140 has the two lens groups 144, 146 that have positive power. The relay lens device 140 is structured by the two lens groups 144, 146 such that the position of the vertical scanning section 120 and the position of the horizontal scanning section 142 are conjugate. More specifically, the relay lens device 140 is structured such that the central positions of the angular scanning of the both scanning sections are conjugate. Further, the relay lens device 140 is structured so as to include a position that is conjugate with the fundus of the subject eye 12. Moreover, the relay lens device 140 is structured such that the position of the vertical scanning section 120 and the position of the horizontal scanning section 142 are conjugate with the pupil of the subject eye 12.

The light that exits from the SLO unit 18 is two-dimensionally scanned by the vertical scanning section 120 and the horizontal scanning section 142 that structure the SLO optical system. The SLO laser light that is scanned two-dimensionally is made incident on the subject eye 12 via the objective lens 1130. The SLO laser light that is reflected by the subject eye 12 goes through the objective lens 1130, the horizontal scanning section 142, the relay lens device 140 and the vertical scanning section 120, and is made incident on the SLO unit 18.

The objective lens 1130 has, in order from the horizontal scanning section 142 side, the first lens group G1 and the second lens group G2. At least the second lens group G2 is a positive lens group having positive power overall. In the present embodiment, the first lens group G1 also is a positive lens group having positive power overall. Each of the first lens group G1 and the second lens group G2 has at least one positive lens. In a case in which each of the first lens group G1 and the second lens group G2 has plural lenses, the first lens group G1 and the second lens group G2 may include a negative lens, provided that each of the first lens group G1 and the second lens group G2 has positive power overall. The objective lens 1130 is structured to include a position that is conjugate with the fundus of the subject eye 12.

Due to the above-described structure, an ophthalmic device that is exclusively used for SLO can be provided.

Second Structural Example

At the ophthalmic device that serves as a second structural example, chromatic aberration correction in at least the visible region for SLO is carried out at the objective lens. An optical system, which includes an objective lens at which this chromatic aberration correction in the visible region is carried out, is described.

FIG. 19 illustrates an example of the structure of an imaging optical system 116C in the ophthalmic device relating to the second structural example.

As illustrated in FIG. 19, the ophthalmic device relating to the second structural example has functions of being able to work for both SLO and OCT. Further, the ophthalmic device relating to the second structural example includes an alignment optical system. Specifically, the optical system that functions as SLO is used as the reference, and the imaging optical system 116C includes, in order from the subject eye 12 side, the objective lens 1130 at which chromatic aberration correction in the visible region is carried out, the horizontal scanning section (H scanner) 142, the relay lens device 140 for SLO, and the vertical scanning section (V scanner) 120 such as a polygon mirror or the like.

As described above, because the wavelengths of the lights that are used are different in an optical system for SLO and an optical system for OCT, it is preferable to adjust the lens structures to as to accord with them respectively. In the second structural example, because the optical system for SLO and the optical system for OCT are used at the shared objective lens 1130, the difference in aberration correction is absorbed at the relay lens device. Specifically, the relay lens device is structured by two lens groups, and the front lens group (e.g., the lens group 144 that is at the objective lens 1130 side of a relay lens device 1140 for SLO) is used in common, and, by making the structure of a lens group 1146 at the scanner 142 side be a structure that is different than a lens group 1146A at the OCT side, the system is structured so as to switch from functioning as a relay lens device for SLO to functioning as a relay lens device for OCT. Further, the scanning section that scans OCT light also is different. Therefore, the second structural example has, between the objective lens 1130 and the horizontal scanning section (H scanner) 142, the relay lens device 1140 that has a structure similar to the relay lens device 140 for SLO. The relay lens device 1140 has, in order from the subject eye 12 side, a front side lens group 1144 and the rear side lens group 1146, and has, between the lens groups 1144, 1146, a beam splitter 1148 that reflects the OCT light and the reflected light from the fundus. Specifically, the relay lens device 1140 has the lenses 1144, 1146 that have plural positive powers in the same way as the relay lens device 140, and is structured to include a position that is conjugate with the fundus of the subject eye 12. The lens group 1146A, which corresponds to the lens group 1146 at the relay lens device 1140 for SLO and at which aberration correction for OCT is carried out, and a scanning section 1142 for OCT are disposed in that order at the opposite side of the beam splitter 1148, i.e., the side opposite the reflected light from the fundus. Namely, this is a structure in which, in OCT, XY scanning is executed independently from SLO. Further, the scanning section 1142 for OCT is disposed at a position that is conjugate with the pupil of the subject eye 12.

Further, in order for the imaging optical system 116C to include an alignment optical system, the imaging optical system 116C has, between the objective lens 1130 and the relay lens device 1140, the beam splitter 178 that guides the optical path with respect to an alignment optical system 138H. Namely, at the imaging optical system 116C, the beam splitter 178 is inserted on the optical path of the optical system that functions as SLO, and the alignment optical system, which includes a fixation target projecting optical system 138HA, an subject eye position imaging optical system 138HB and an illuminating device 138HC, is provided at the opposite side of the beam splitter 178. Further, the beam splitter 178 is disposed at a position that is conjugate with the pupil of the subject eye 12.

Due to the above-described structure, the objective lens 1130 for SLO can also be used for OCT.

Third Structural Example

An ophthalmic device that serves as a third structural example is an ophthalmic device used exclusively for OCT that uses, as the objective lens for OCT, an objective lens at which chromatic aberration correction in at least the visible region is carried out for SLO.

FIG. 20 illustrates an example of the structure of an imaging optical system 116D in the ophthalmic device relating to the third structural example.

As illustrated in FIG. 20, the ophthalmic device relating to the third structural example functions as a device exclusively used for OCT. Specifically, the imaging optical system 116D has, in order from the subject eye 12 side, the objective lens 1130 at which chromatic aberration correction in the visible region is carried out, the relay lens device 1140 that includes the beam splitter 1148, the lens group 1146A at which aberration correction is carried out for OCT and that is at the opposite side of the beam splitter 1148, and the scanning section 1142 for OCT. The imaging optical system 116D has fundus camera optical system Fundus at the transmission side of the relay lens device 1140. The fundus camera optical system Fundus is disposed at a position that is conjugate with the pupil of the subject eye 12.

Due to the above-described structure, an ophthalmic device that is used exclusively for OCT can be provided by using the objective lens 1130 for SLO.

Fourth Structural Example

An ophthalmic device that serves as a fourth structural example is an ophthalmic device for SLO that has the objective lens 130 relating to the first embodiment, i.e., the objective lens 130 at which chromatic aberration correction in the visible region and the near infrared region is carried out.

FIG. 21 illustrates an example of the structure of an imaging optical system 116E in the ophthalmic device relating to the fourth structural example.

As illustrated in FIG. 21, the ophthalmic device relating to the fourth structural example functions as a device exclusively used for SLO. Specifically, the imaging optical system 116E has, in order from the subject eye 12 side, the objective lens 130 relating to the first embodiment, i.e., the objective lens 130 at which chromatic aberration correction in the visible region and the near infrared region is carried out, the horizontal scanning section 142, the relay lens device 140 and the vertical scanning section 120.

As explained in FIG. 3, the objective lens 130 has, in order from the horizontal scanning section 142 side, the first lens group G1 and the second lens group G2, and has the third lens group G3 between the first lens group G1 and the second lens group G2. The objective lens 130 is structured so as to include a position that is conjugate with the pupil of the subject eye 12 within the third lens group G3, and further, is structured so as to include a position that is conjugate with the fundus of the subject eye. Note that, in FIG. 21, the three lens groups within the objective lens 130 are illustrated simply as G1, G2, G3. These correspond to the three lens groups 134, 132, 133 illustrated in FIG. 3. The same holds in the drawings hereinafter.

In this way, by using the objective lens 130 that incorporates an intermediate pupil therein, chromatic aberration correction in the visible region and the near infrared region is carried out, and the maximum aperture of the objective lens 130 is reduced, and an increase in the weight of the objective lens 130 is suppressed. Due thereto, there can be provided an ophthalmic device used exclusively for SLO in which the weight of the device overall can be lightened.

Fifth Structural Example

An ophthalmic device that serves as a fifth structural example is an ophthalmic device having SLO and OCT, and having the objective lens 130 at which chromatic aberration correction in the visible region and the near infrared region is carried out.

FIG. 22 illustrates an example of the structure of an imaging optical system 116F in the ophthalmic device relating to the fifth structural example. As illustrated in FIG. 22, the ophthalmic device relating to the fifth structural example has functions of being able to work for both SLO and OCT. In the fifth structural example that is illustrated in FIG. 22, the point that the objective lens 1130 of the second structural example illustrated in FIG. 19 is replaced with the objective lens 130, at which chromatic aberration correction in the visible region and the near infrared region is carried out, is different.

Due to the above-described structure, an objective lens for SLO and an objective lens for OCT can be used in common.

Sixth Structural Example

An ophthalmic device that serves as a sixth structural example is an ophthalmic device used exclusively for OCT that uses, as the objective lens for OCT, the objective lens 130 at which chromatic aberration correction in the visible region and the near infrared region is carried out.

FIG. 23 illustrates an example of the structure of an imaging optical system 116G in the ophthalmic device relating to the sixth structural example.

As illustrated in FIG. 23, the ophthalmic device relating to the sixth structural example functions as a device used exclusively for OCT. In the sixth structural example illustrated in FIG. 23, the point that the objective lens 1130 of the third structural example illustrated in FIG. 20 is replaced with the objective lens 130 at which chromatic aberration correction in the visible region and the near infrared region is carried out, differs. In this structure, as explained in FIG. 3, at the objective lens 130, aberration correction for both the SLO optical system and the OCT optical system is carried out by the aberration correcting ability of the third lens group 133 (G3) that serves as an intermediate group, and therefore, the structures of the relay lenses can be made to be exactly the same structures.

Due to the above-described structure, an ophthalmic device, which is exclusively used for OCT and in which chromatic aberration correction is carried out from the visible region to the near infrared region, can be provided.

Seventh Structural Example

An ophthalmic device that serves as a seventh structural example is an ophthalmic device that functions as both SLO and OCT, and uses the objective lens 130 at which chromatic aberration correction in the visible region and the near infrared region is carried out.

FIG. 24 illustrates an example of the structure of an imaging optical system 116H in the ophthalmic device relating to the seventh structural example.

As illustrated in FIG. 24, the ophthalmic device relating to the seventh structural example functions as a SLO device and an OCT device. Specifically, the imaging optical system 116H has, in order from the subject eye 12 side, the objective lens 130 at which chromatic aberration correction from the visible region to the near infrared region is carried out and that includes the first lens group G1 through the third lens group G3, and has the horizontal scanning section 142, the relay lens device 140 and the vertical scanning section 120, and structures an optical system for SLO.

In order to absorb the difference in aberration correction that is due to the difference in the scanning lights of SLO and OCT, in the seventh structural example, the optical system for SLO is used as the reference, and the system is structured so as to also accord with an optical system for OCT by adjusting the structure of the first lens group G1 of the objective lens 130 (refer to FIG. 16 as well). Namely, the system is structured so as to propagate substantially parallel light between the first lens group G1 and the third lens group G3, and the splitting/combining element (e.g., a dichroic mirror) DM1 is disposed on the optical path thereof. A lens group 134A, which corresponds to the first lens group G1 of the objective lens that functions as SLO and at which aberration correction is carried out for OCT, and a scanning section 1142A for OCT, are disposed in that order at the opposite side of the splitting/combining element DM1. Namely, this is a structure in which, in OCT, XY scanning is executed independently of SLO. Further, the scanning section 1142A for OCT is disposed at a position that is conjugate with the pupil of the subject eye 12. By structuring the system in this way, the two optical systems for SLO and OCT can be combined, while taking the aberrations of the individual optical systems into consideration.

Further, the ophthalmic device of the seventh structural example has the alignment optical system 138H. Specifically, a prism for optical path combining is disposed at either one of the front and rear regions of the pupil conjugate position P3 that is within the third lens group G3. In the example illustrated in FIG. 24, a case is illustrated in which the prism for optical path combining is disposed in front of the pupil conjugate position (the region where the splitting/combining element DM1 illustrated in FIG. 16 is disposed). By structuring the system in this way, at least one optical system among the fixation target projecting optical system 138HA and the subject eye position imaging optical system 138HB can be placed appropriately.

Due to the above-described structure, an ophthalmic device that functions respectively as SLO and OCT at which aberration correction is carried out appropriately can be provided, and an ophthalmic device having the alignment optical system 138H can be provided.

In this way, because the technique relating to the seventh embodiment includes the providing of an ophthalmic device including at least one of SLO, OCT and alignment optical systems, this technique includes the following second technique.

(Second Technique)

An ophthalmic device having:
  a first scanning section for scanning a light bundle that is from a first light source;
  an afocal objective lens system that guides the light bundle scanned by the first scanning section to an subject eye;
  a first optical path disposed between the first scanning section and the objective lens, and having a first afocal relay system that guides the light bundle scanned from the first scanning section to the objective lens;
  a second scanning section for scanning a light bundle that is from a second light source that is different than the first light source; and
  a second optical path having a second afocal relay system for passing the light bundle, which was scanned by the second scanning section, through the afocal objective lens system and guiding the light bundle to the subject eye,
wherein the first afocal relay system and the second afocal relay system have a shared beam splitter, and the first optical path and the second optical path are combined by the shared beam splitter.

Further, the technique of the present disclosure includes the following third technique.

(Third Technique)

The ophthalmic device of the second technique, wherein the first afocal relay system and the second afocal relay system have two positive lens groups respectively, and the shared beam splitter is disposed between the two positive lens groups, and the positive lens group, which is at the shared afocal objective lens system side of the first afocal relay system, is structured so as to be used in common as the positive lens group that is at the shared afocal objective lens system side of the second afocal relay system.

By the way, as described above, cases of using an objective lens in common for SLO and OCT respectively, and cases in which aberration correction is carried out for only either one light source of SLO and OCT and it is considered that the aberration correction of the other is insufficient, are included. Therefore, the technique of the present disclosure includes the following fourth technique.

(Fourth Technique)

The ophthalmic device of the second technique, wherein the positive lens group at the first scanner side of the first afocal relay system is different than the positive lens group at the second scanner side of the second afocal relay system, at the first optical path, at a combined system of the first afocal relay system and the shared objective lens system, aberration correction is carried out on the light bundle from the first light source, at the second optical path, at a combined system of the second afocal relay system and the shared objective lens system, aberration correction is carried out on the light bundle from the second light source.

Further, because the technique of the present disclosure includes a case in which aberration correction is complete at the shared objective lens system, the following fifth technique is included.

(Fifth Technique)

The ophthalmic device of the second technique, wherein at the shared objective lens system, aberration correction is carried out on the light bundle from the first light source and on the light bundle from the second light source, the positive lens group at the first scanner side of the first afocal relay system is the same as the positive lens group at the second scanner side of the second afocal relay system, at the first optical path, at a combined system of the first afocal relay system and the shared objective lens system, aberration correction is carried out on the light bundle from the first light source, and at the second optical path, in combining the second afocal relay system and the shared objective lens system, aberration correction is carried out on the light bundle from the second light source.

Further, because the technique of the present disclosure includes a case in which the shared objective lens system is an objective lens in which a pupil is incorporated, the following sixth technique is included.

(Sixth Technique)

The ophthalmic device of the second technique, wherein the shared objective lens system has:

a positive first lens group G1 at the scanner side;

a positive second lens group G2 at the subject eye side; and a third lens group G3 that is disposed between the both groups and includes a diverging surface.

Further, the technique of the present disclosure includes the following seventh technique.

(Seventh Technique)

The ophthalmic device of the second technique, wherein, at the shared objective lens system, a conjugate position (intermediate pupil position) that is conjugate with the scanning center of the scanner is formed between the first lens group G1 and the second lens group G2, and the third lens group G3 includes this intermediate pupil position.

Further, the technique of the present disclosure includes the following eighth technique.

(Eighth Technique)

An ophthalmic device having:

a first scanner for scanning a light bundle that is from a first light source;

an afocal objective lens system that guides the light bundle scanned by the first scanning section to an subject eye;

a first optical system disposed between the first scanning section and the afocal objective lens, and having a first afocal relay system that guides the light bundle scanned from the first scanning section to the afocal objective lens;

a second scanning section for scanning a light bundle that is from a second light source that is different than the first light source; and a second optical system having a second afocal relay system for passing the light bundle, which was scanned by the second scanning section, through the afocal objective lens system and guiding the light bundle to the subject eye, wherein the second afocal relay system has a beam splitter, and is structured so as to be able to be switched with the first afocal relay system, and, by switching the first afocal relay system to the second afocal relay system, the first optical system and the second optical system are combined via the beam splitter, and subject eye observation by the first light source and subject eye observation by the second light source become possible.

Further, the technique of the present disclosure includes the following ninth technique.

(Ninth Technique)

The ophthalmic device of the eighth technique, wherein, at the shared objective lens system, aberration correction is carried out on the light bundle from the first light source and the light bundle from the second light source, and the first afocal relay system and the second afocal relay system are the same.

Further, the technique of the present disclosure includes the following tenth technique.

(Tenth Technique)

The ophthalmic device of the eighth technique, wherein the shared objective lens system has:

a positive first lens group G1 at the scanner side;

a positive second lens group G2 at the subject eye side; and a third lens group G3 that is disposed between the both groups and includes a diverging surface.

Although the technique of the present disclosure has been described by using embodiments, the technical scope of the present disclosure is not limited to the scope put forth in the above-described embodiments. Various modifications and improvements can be added to the above-described embodiments within a scope that does not depart from the gist of the invention, and forms to which such modifications and improvements have been added also are included in the technical scope of the present disclosure. Further, all publications, patent applications, and technical standards mentioned in the present specification are incorporated by reference into the present specification to the same extent as if such individual publication, patent application, or technical standard was specifically and individually indicated to be incorporated by reference.

EXPLANATION OF REFERENCE NUMERALS

110 ophthalmic device
17 image processing device
20C first optical coupler
40, 42, 44, 46 light source
70, 72, 74, 76 light detecting elements
132 second lens group
133 third lens group
134 first lens group
142 horizontal scanning section
148 vertical scanning section

The invention claimed is:

1. An ophthalmic device for observing a subject eye, the device comprising:
a light source;
a scanning section that scans light from the light source; and
an objective optical system configured to form a pupil, which has a conjugate relationship with a pupil of the subject eye, at the scanning section,
wherein the objective optical system has, in order from the scanning section toward the subject eye,
a first lens group that is positive,
a second lens group that is positive, and
a third lens group that is disposed between the first lens group and the second lens group, and that includes a concave surface configured to diverge light,
wherein, the objective optical system forms an intermediate pupil, which has a conjugate relationship with the pupil of the subject eye, is formed between the first lens group and the second lens group, and the third lens group is disposed so as to include a position of the intermediate pupil, and
wherein, when W1 represents a distance between a lens surface, which is furthest from the subject eye in the first lens group, and a position of the scanning section, W2 represents a distance between a lens surface, which is nearest to a side of the subject eye of the second lens group, and the pupil of the subject eye, and D represents a distance between a concave surface, which has the most power in the third lens group, and the position of the intermediate pupil, the objective optical system satisfies the following conditions:

$D<W1$ $D<W2.$

2. The ophthalmic device of claim 1, wherein, at the objective optical system, when R represents a radius of curvature of a lens surface, N represents a refractive index of an incident side of the lens surface, and N' represents a refractive index of an exiting side of the lens surface, a Petzval curvature is a value determined by the following equation:

$C=\{(1/N')-(1/N)\}/(-R)$ and
when C1 represents the Petzval curvature of a diverging lens surface that is nearest to a pupil position that has a conjugate relationship with the pupil of the subject eye in the first lens group of the objective optical system, C2 represents the Petzval curvature of a lens surface that is nearest to the subject eye in the second lens group, and C3 represents the Petzval curvature of a concave surface that has the most power in the third lens group, the following conditional expressions are satisfied:

$C3<C1$ $C3<C2.$

3. The ophthalmic device of claim 1, wherein an air gap between the first lens group and the third lens group, and an air gap between the third lens group and the second lens group are, among lens gaps of the objective lens overall, the largest air gap and the next largest air gap.

4. An ophthalmic device for observing a subject eye, the device comprising:
a light source;
a scanning section that scans light from the light source; and
an objective optical system configured to form a pupil, which has a conjugate relationship with a pupil of the subject eye, at the scanning section,
wherein the objective optical system has, in order from the scanning section toward the subject eye,
a first lens group that is positive,
a second lens group that is positive, and
a third lens group that is disposed between the first lens group and the second lens group, and that includes a concave surface configured to diverge light, and
wherein, when φ1 represents a maximum effective diameter of lenses included in the first lens group, φ2 represents a maximum effective diameter of lenses included in the second lens group, and φ3 represents a maximum effective diameter of lenses included in the third lens group, the following conditional expression is satisfied:

$φ3, φ1 < 0.7*φ2.$

5. An ophthalmic optical system for observing a subject eye, the system comprising an objective optical system configured to form a pupil having a conjugate relationship with a pupil of the subject eye,
wherein the objective optical system has, in order from a side at which the pupil having a conjugate relationship with the pupil of the subject eye is formed, toward the subject eye,
a first lens group that is positive,
a second lens group that is positive, and
a third lens group that includes a concave surface configured to diverge light and that is disposed between the first lens group and the second lens group,
wherein, at the objective optical system, an intermediate pupil, which has a conjugate relationship with the pupil of the subject eye, is formed between the first lens group and the second lens group, and the third lens group is disposed so as to include a position of the intermediate pupil, and
wherein, when W1 represents a distance between a lens surface, which is furthest from the subject eye in the first lens group, and a pupil position having a conjugate relationship with the pupil of the subject eye, W2 represents a distance between a lens surface, which is nearest to the subject eye side of the second lens group, and the pupil of the subject eye, and D represents a distance between a concave surface, which has the strongest diverging power among concave lenses in the third lens group, and the position of the intermediate pupil, the objective optical system satisfies the following conditions:

$$D<W1$$

$$D<W2.$$

6. The ophthalmic optical system of claim 5, wherein, at the objective optical system, when R represents a radius of curvature of a lens surface, N represents a refractive index of an incident side of the lens surface, and N' represents a refractive index of an exiting side of the lens surface, a Petzval curvature is a value determined by the following equation:

$$C=\{(1/N')-(1/N)1/(-R)$$

and when C1 represents the Petzval curvature of a diverging lens surface that is nearest to a pupil position that has a conjugate relationship with the pupil of the subject eye in the first lens group of the objective optical system, C2 represents the Petzval curvature of a lens surface that is nearest to the subject eye in the second lens group, and C3 represents the Petzval curvature of a concave surface that has the most power in the third lens group, the following conditional expressions are satisfied:

$$C3<C1$$

$$C3<C2.$$

7. The ophthalmic optical system of claim 5, wherein a gap between the first lens group and the third lens group, and an air gap between the third lens group and the second lens group are, among lens gaps of the objective lens overall, the largest air gap and the next largest air gap.

8. An ophthalmic optical system for observing a subject eye, the system comprising an objective optical system configured to form a pupil having a conjugate relationship with a pupil of the subject eye,
wherein the objective optical system has, in order from a side at which the pupil having a conjugate relationship with the pupil of the subject eye is formed, toward the subject eye,
a first lens group that is positive,
a second lens group that is positive, and
a third lens group that includes a concave surface configured to diverge light and that is disposed between the first lens group and the second lens group,
wherein, when $\varphi 1$ represents a maximum effective diameter of lenses included in the first lens group, $\varphi 2$ represents a maximum effective diameter of lenses included in the second lens group, and $\varphi 3$ represents a maximum effective diameter of lenses included in the third lens group, the following conditional expression is satisfied:

$$\varphi 3, \varphi 1<0.7*\varphi 2.$$

* * * * *